United States Patent
Yoshida et al.

(10) Patent No.: US 10,765,392 B2
(45) Date of Patent: Sep. 8, 2020

(54) X-RAY IMAGING APPARATUS AND X-RAY IMAGE DISPLAY METHOD

(71) Applicant: Shimadzu Corporation, Kyoto (JP)

(72) Inventors: Koki Yoshida, Kyoto (JP); Takanori Yoshida, Kyoto (JP); Michel Dargis, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 231 days.

(21) Appl. No.: 15/962,488

(22) Filed: Apr. 25, 2018

(65) Prior Publication Data

US 2018/0310905 A1 Nov. 1, 2018

(30) Foreign Application Priority Data

Apr. 25, 2017 (JP) ................................ 2017-086251

(51) Int. Cl.
| | |
|---|---|
| *G06K 9/00* | (2006.01) |
| *A61B 6/00* | (2006.01) |
| *G06T 7/00* | (2017.01) |
| *G06T 3/40* | (2006.01) |

(Continued)

(52) U.S. Cl.
CPC ............ *A61B 6/5205* (2013.01); *A61B 6/487* (2013.01); *A61B 6/503* (2013.01); *G06T 3/403* (2013.01); *G06T 7/0014* (2013.01); *G06T 7/246* (2017.01); *A61B 6/0492* (2013.01); *A61B 6/504* (2013.01); *G06T 2207/10121* (2013.01); *G06T 2207/30048* (2013.01); *G06T 2207/30204* (2013.01)

(58) Field of Classification Search
CPC ....... A61B 6/5205; A61B 6/503; A61B 6/487; A61B 6/504; A61B 6/0492; G06T 7/246; G06T 3/403; G06T 7/0014; G06T 2207/10121; G06T 2207/30204; G06T 2207/30048
USPC ........................................................ 382/132
See application file for complete search history.

(56) References Cited

U.S. PATENT DOCUMENTS

| | | | |
|---|---|---|---|
| 6,097,833 A | * | 8/2000 | Lobregt ................. A61B 6/481 348/E5.089 |
| 8,655,042 B2 | | 2/2014 | Florent |

(Continued)

FOREIGN PATENT DOCUMENTS

| | | |
|---|---|---|
| JP | 2012-531236 A | 12/2012 |
| JP | 2017-094006 A | 1/2017 |
| WO | 2015030091 A1 | 3/2015 |

OTHER PUBLICATIONS

Notice of Reasons for Refusal, dated Jun. 2, 2020, issued by the Japanese Patent Office for corresponding Japanese Patent Application No. 2017-086251, with English language machine translation thereof (13 pages).

*Primary Examiner* — Van D Huynh
(74) *Attorney, Agent, or Firm* — Muir Patent Law, PLLC

(57) ABSTRACT

This X-ray imaging apparatus is equipped with an image processing unit. The image processing unit obtains a first image with a marker reference position set in a first X-ray image and generate a second image in which a virtual marker image is superimposed at a corresponding position in a second X-ray image reflecting the change of a relative position from the marker reference position with respect to the second X-ray image different from the first X-ray image.

22 Claims, 12 Drawing Sheets

(51) Int. Cl.
*G06T 7/246* (2017.01)
*A61B 6/04* (2006.01)

(56) References Cited

U.S. PATENT DOCUMENTS

| | | | | |
|---|---|---|---|---|
| 8,977,028 B2* | 3/2015 | Moon | ............ | G06T 11/60 |
| | | | | 382/131 |
| 2009/0190808 A1* | 7/2009 | Claus | ............ | A61B 3/0041 |
| | | | | 382/128 |
| 2010/0195887 A1* | 8/2010 | Abe | ............ | G06T 7/246 |
| | | | | 382/131 |
| 2011/0109650 A1* | 5/2011 | Kreeger | ............ | G16H 50/50 |
| | | | | 345/634 |
| 2011/0188726 A1* | 8/2011 | Nathaniel | ............ | A61B 6/025 |
| | | | | 382/132 |
| 2015/0335305 A1* | 11/2015 | Moon | ............ | A61B 6/5294 |
| | | | | 378/98.5 |
| 2016/0350925 A1* | 12/2016 | Moon | ............ | A61B 6/5241 |
| 2017/0154416 A1 | 6/2017 | Dargis et al. | | |

* cited by examiner

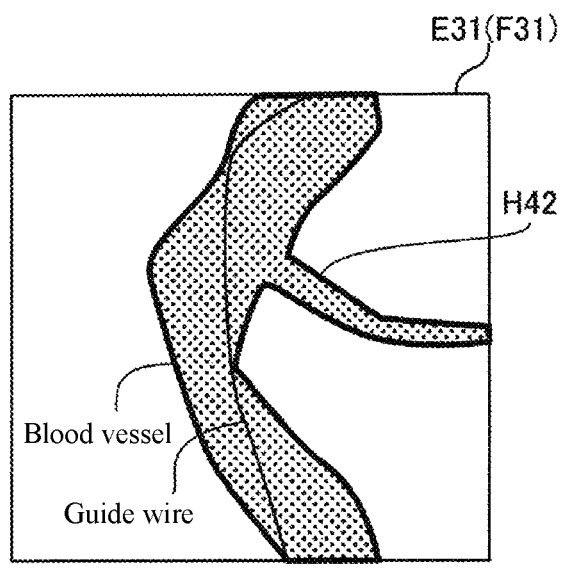 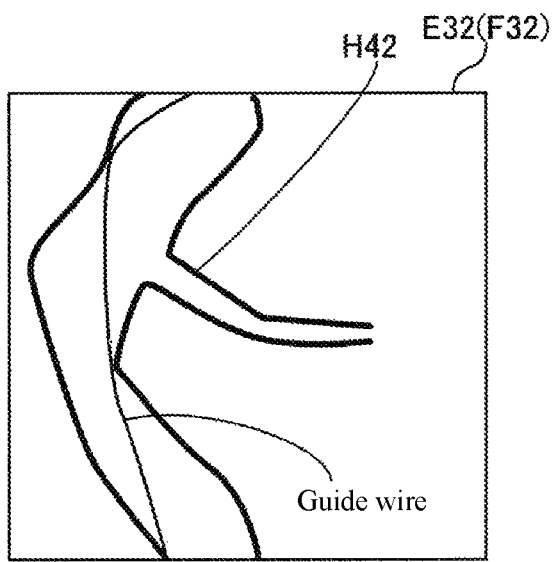
FIG. 19A     FIG. 19B

X-RAY IMAGING APPARATUS AND X-RAY IMAGE DISPLAY METHOD

CROSS-REFERENCE TO RELATED APPLICATIONS

The priority application number JP2017-086251, entitled "X-ray imaging apparatus and X-ray image display method", filed on Apr. 25, 2017 invented by Koki Yoshida, Takanori Yoshida, and Michel Dargis, upon which this patent application is based is hereby incorporated by reference.

BACKGROUND OF THE INVENTION

Field of the Invention

The present invention relates to an X-ray imaging apparatus and an X-ray image display method, and more particular to an X-ray imaging apparatus and an image processing apparatus provided with an image processing unit.

Description of Background Technique

Conventionally, an X-ray imaging apparatus equipped with an image processing unit and an X-ray image display method are known. Such an X-ray imaging apparatus and an X-ray image display method are disclosed in, for example, Japanese Translation of PCT International Application Publication No. 2012-531236.

Japanese Translation of PCT International Application Publication No. 2012-531236 discloses an X-ray imaging system (X-ray imaging apparatus) that performs image processing on an angiographic image. In this X-ray imaging system, an angiographic image (X-ray image) is acquired in a state in which a wire chip having a marker that does not transmit X-rays is placed in a subject. In this X-ray imaging system, it is configured such that an X-ray image of a wire chip in a subject is acquired from an angiographic image, a pseudo ruler (ruler image) extending in parallel to the acquired X-ray image of the wire chip is superimposed on the angiographic image, and the superimposed image is displayed on the display unit. Note that the "ruler image" is an image of a ruler including an image showing a scale.

Further, an X-ray imaging apparatus for X-ray imaging a lower limb portion of a subject has been conventionally known. In this conventional X-ray imaging apparatus, it is configured such that a platform on which a subject is placed and an imaging unit are moved relative to each other so as to move a portion to be imaged with respect to the imaging unit. That is, in the conventional X-ray imaging apparatus, the display position of the region-of-interest changes on the screen of the display unit in accordance with the relative movement of the platform and the imaging unit.

In addition, conventionally, an X-ray imaging apparatus for performing X-ray imaging of a heart part of a subject is known. This conventional X-ray imaging apparatus is configured to image a heart portion of a subject as a moving image. Since a heart always moves due to the heartbeat, the position of the region-of-interest of the heart changes with respect to the imaging unit during the capturing of the moving image. That is, in the conventional X-ray imaging apparatus, as a heart beats, the display position of the region-of-interest of the heart part changes on the screen of the display unit.

Here, in a conventional X-ray imaging apparatus for X-ray imaging a lower limb portion of a subject or a conventional X-ray imaging apparatus for X-ray imaging a heart part of a subject, in order to allow a surgeon to visually recognize a position and a length of a region-of-interest, it is conceivable to add a configuration for making the display unit display a pseudo ruler (ruler image) described in Japanese Translation of PCT International Application Publication No. 2012-531236. However, in an X-ray imaging apparatus to which the configuration for displaying the pseudo ruler is added, when one of the imaging unit and the subject (region-of-interest) moves relative to the other, the display position of the region-of-interest changes on the screen of the display unit. For this reason, there is a disadvantage that the position of the region-of-interest changes with respect to the display position of the pseudo ruler. Therefore, in the conventional X-ray imaging apparatus, when one of the imaging unit and the subject (region-of-interest) moves with respect to the other, even if a pseudo ruler (virtual marker image) is used, there is a problem that a surgeon (operator) cannot visually recognize the accurate position of the region-of-interest.

SUMMARY OF THE INVENTION

The present invention has been made to solve the aforementioned problems, and one of the objects of the present invention is to provide an X-ray imaging apparatus and an X-ray image display method capable of allowing an operator to visually recognize a correct location of a region-of-interest in a subject using a virtual marker image even when one of an imaging unit and a subject (region-of-interest) moves with respect to the other.

In order to attain the aforementioned object, an X-ray imaging apparatus according to a first aspect of the present invention includes an imaging unit configured to capturing an X-ray image by irradiating X-rays to a subject and detecting the X-rays that have passed through the subject, a display unit configured to display the X-ray image, and an image processing unit configured to process the X-ray image captured by the imaging unit. The image processing unit is configured to obtain a first image in which a marker reference position is set in a first X-ray image and generate a second image in which a virtual marker image is superimposed with respect to a second X-ray image captured separately from the first X-ray image and different in a relative position between the subject and the imaging unit from the first X-ray image at a corresponding position in the second X-ray image reflecting a change of the relative position from the marker reference position. The second image is configured to be displayed on the display unit. Note that the wording "virtual" in the "virtual marker image" means to display a virtual (pseudo) marker image in addition to an X-ray imaged real image.

In the X-ray imaging apparatus according to the first aspect of the present invention, as described above, the image processing unit is configured to obtain a first image in which a marker reference position is set in a first X-ray image and generate a second image in which a virtual marker image is superimposed on a second X-ray image captured separately from the first X-ray image and different in a relative position between the subject and the imaging unit from the first X-ray image at a corresponding position in the second X-ray image reflecting a change of the relative position from the marker reference position. With this, even in cases where the position of the region-of-interest in the X-ray image at the time of capturing the first X-ray image and the position of the region-of-interest of the X-ray image at the time of capturing the second X-ray image are different, it is possible to properly display the virtual marker image at the corresponding position (the position of the region-of-interest) in the second image. As a result, even when one of the imaging unit and the subject (region-of-interest) moves with respect to the other, the virtual marker image enables the operator to visually recognize the accurate position of the region-of-interest in the subject. As a result, if imaging is performed in a state in which a contrast agent is injected at the position of the region-of-interest of the subject at the time of capturing the first X-ray image, it becomes possible to allow the operator to visually recognize the accurate position of the region-of-interest in the subject by the virtual marker image without injecting a contract medium again at the time of capturing the second X-ray image. Therefore, the contrast agent usage can be reduced.

In the X-ray imaging apparatus according to the first aspect of the present invention, preferably, the virtual marker image includes a pair of virtual marker images. With this configuration, unlike a virtual marker image showing one point, it is possible to allow the operator to visually recognize the arrangement relation between the pair of virtual marker images. For example, it is possible to allow the operator to visually recognize the distance between the pair of virtual marker images.

In the X-ray imaging apparatus according to the first aspect of the present invention, preferably, the virtual marker image includes a virtual ruler image. With this configuration, it is possible to allow the operator to visually recognize the distance on the second image by using the virtual ruler image. In addition, if the virtual ruler image is displayed along the shape of a blood vessel, even if the blood vessel is not imaged in the second image, it is possible to allow the operator to visually recognize the shape of the blood vessel.

In the X-ray imaging apparatus according to the first aspect of the present invention, preferably, the image processing unit is configured to perform image processing of superimposing the virtual marker image at the marker reference position in the first image with respect to the first image. With this configuration, it is possible to allow the operator to visually recognize the marker reference position in the first image by the virtual marker image displayed on the first image.

In the X-ray imaging apparatus according to the first aspect of the present invention, preferably, the image processing unit is configured to acquires the change of the relative position based on movement information of at least one of the subject and the imaging unit and generate the second image in which the virtual marker image is superimposed at the corresponding position in the second X-ray image reflecting the acquired relative position change. With this configuration, by acquiring the movement information of at least one of the subject and the imaging unit, it is possible to easily acquire the change of the relative position between the subject and the imaging unit.

In this case, preferably, the imaging unit includes an X-ray irradiation detection unit configured to irradiate X-rays to the subject and detect the X-rays that have passed through the subject, and a placement unit for placing a subject thereon, wherein at least one of the X-ray irradiation detection unit and the placement unit is configured to be movable with respect to the other, and the image processing unit is configured to acquire the change of the relative position based on the movement information of at least one of the X-ray irradiation detection unit and the placement unit. With this configuration, by acquiring the movement information of at least one of the X-ray irradiation detection unit and the placement unit, it is possible to acquire the information on the positional change of the imaging unit with respect to the subject. As a result, for example, by fixing the image capturing part of the subject to the placement unit at the time of image capturing, it is possible to acquire the change of the relative position between the subject and the imaging unit without acquiring the movement information of the subject. Therefore, it is possible to suppress the increase in the burden of processing in the image processing unit.

In the X-ray imaging apparatus for acquiring the change of the relative position based on the movement information of at least one of the subject and the imaging unit, preferably, the image processing unit is configured to acquire the movement information as the movement information of the subject from a position of a first feature point in the subject in the first X-ray image to a position of the first feature point in the subject in the second X-ray image, and acquire the change of the relative position based on the acquired movement information. With this configuration, even if the region-of-interest of the subject moves with respect to the imaging unit with the imaging unit not moved, the change of the relative position between the imaging unit and the subject can be acquired by obtaining the movement information of the subject by acquiring the position of the first feature point in the first image.

In this case, preferably, the first feature point includes at least one of an indwelling object in the subject and a structural object of the subject. With this configuration, since at least one of the indwelling object in the subject and the structural object of the subject which are hard to transmit X-rays and easy to be visually recognized (detected) as compared with blood vessels on the X-ray image is included in the first feature point, it is possible to easily acquire the position of the first feature point from the first X-ray image.

In the X-ray imaging apparatus for acquiring the movement information of the first feature point, preferably, the first image is a moving image in which a periodically moving subject is image-captured, and the image processing unit is configured to acquire periodic movement information of the first feature point in the subject in the first image and periodic movement information of the marker reference position and acquire the change of the relative position based on the acquired periodic movement information. With this configuration, in the case of X-ray imaging a periodically moving part of a subject (heart part or the like), based on the information of the periodic movement (e.g., the heartbeat) of the subject in the first X-ray image and the periodic movement information of the marker reference position resulting from the movement of the subject, the corresponding position in the second X-ray image can be acquired (calculated). As a result, even in cases where the subject periodically moves, the virtual marker image can be displayed at an appropriate position in the second image.

In this case, preferably, the image processing unit is configured to generate the first image in which the marker reference position is set based on the position of the second feature point in the subject different from the first feature point in the first X-ray image, acquire the periodic movement information of the first feature point and the periodic movement information of the second feature point, acquire the change of the relative position based on the acquired periodic movement information, and generate the second image in which the virtual marker image virtually displaying the second feature point is superimposed at the corresponding position in the second X-ray image that does not have the second feature point reflecting the change of the relative position. With this configuration, the position of the second feature point in the first X-ray image can be automatically set as the marker reference position, and also for the second image in which the second feature point does not exist, the virtual marker image can be displayed at the position corresponding to the second feature point. As a result, even in cases where the second feature point does not exist in the second image, it is possible to virtually display the position of the second feature point by the virtual marker image at an appropriate position.

In the X-ray imaging apparatus for acquiring the periodic movement information of the second feature point, preferably, the second feature point includes an indwelling object in the subject. With this configuration, even in a state in which the indwelling object is placed in the subject at the time when the first X-ray image was captured and in a state in which the indwelling object has been removed from the subject or the indwelling object has not yet been placed in the subject at the time when the second X-ray image was captured, the indwelling position of the indwelling object can be virtually displayed in the second image by the virtual marker image.

In the X-ray imaging apparatus for acquiring the movement information of the first feature point, preferably, the first image and the second image each include an image in which a heart part of the subject is imaged. With this configuration, since the heart part of the subject is a part of the subject repeating the movement (motion) periodically, even in cases where the subject periodically moves, it is particularly effective to apply the present invention capable of making the region-of-interest visible more appropriately by the virtual marker image to an X-ray imaging apparatus for X-ray imaging a heart part of a subject.

In the X-ray imaging apparatus according to the first aspect of the present invention, preferably, at least one of the first image and the second image is a stitched image captured at a plurality of relative positions. With this configuration, even in cases where the relative position between the stitched image and the other X-ray image is different, the virtual marker image can be displayed at an appropriate position in the second image.

In this case, preferably the first image is a stitched image and the second image is a fluoroscopic image captured at one relative position. In general, when X-ray imaging a lower limb portion of a subject, initially, the stitched image is X-ray imaged, and then the region-of-interest (such as the placement position of the stent) is determined by a surgeon while the stitched image is being visually recognized by the surgeon. Thereafter, one (single) fluoroscopic image is captured at one relative position, and the surgeon preforms a medical treatment of the region-of-interest. Considering this procedure, in the present invention, by configuring as described above, the marker reference position is set in the stitched image, and the virtual marker image can be displaced at the proper position of the region-of-interest in a single fluoroscopic image. Therefore, the convenience for a surgeon (operator) can be improved.

In the X-ray imaging apparatus in which at least one of the first image and the second image is a stitched image, preferably, the first image and the second image each include an image in which a lower limb portion of the subject is imaged. Here, the stitched image is generally generated when a lower limb portion of a subject is X-ray imaged. Considering this point, according to the present invention, by configuring as described above, even in cases where a stitched image of a lower limb portion is X-ray imaged, the region-of-interest can be visually recognized by a virtual marker image at an appropriate position. That is, it is particularly effective to apply the present invention to an X-ray imaging apparatus for X-ray imaging a lower limb portion of a subject.

In the X-ray imaging apparatus according to the first aspect of the present invention, preferably, the second image is a moving image. With this configuration, the operator (surgeon) can perform the operation (medical treatment) with respect to the region-of-interest while visually recognizing the second image as a moving image in which the virtual marker image is displayed in a superimposed manner.

In the X-ray imaging apparatus according to the first aspect of the present invention, preferably, the first image is an image including an image of a contrast agent injected into a subject and the second image is an image not including the image of the contrast agent. Here, when X-ray imaging a subject (living body), X-ray imaging is first performed in a state in which a contrast agent is injected, and the region-of-interest (stent placement position, etc.) is determined by a surgeon while the contrast image is being visually recognized by the surgeon. After that, a medical treatment is performed by a surgeon with respect to a subject in a state in which no contrast agent exists. Considering this procedure, according to the present invention, by configuring as described above, when a surgeon performs a medical treatment on a region-of-interest, it is possible to appropriately display the virtual marker image corresponding to the region-of-interest in the image not including the image of the contrast agent. Note that in the specification of this application, the term "image not including the image of the contrast agent" is described as a broad connect including not only an image which is X-ray imaged in a state in which the contrast agent is not injected at all in the subject but also an image in a state in which it is not displayed in a clearly visible manner as an image of the contrast agent when X-ray imaging even when the contrast agent remains in the subject.

In the X-ray imaging apparatus according to the first aspect, preferably, the first image includes an image in which a partial image in the moving image is displayed as a still image. Here, for example, in the case of a moving image acquired in a state in which the contrast agent is injected into the subject, there is a disadvantage that as the contrast agent flows out of the blood vessel in the imaging region, the contrast agent changes from the state in which the contrast agent is imaging the region-of-interest position to the state in which it is not imaging. In this respect, in the present invention, by configuring as described above, for example, since it is possible to display on the display unit as a still image in a state in which the contrast image is imaging the position near the region-of-interest, it is possible to easily set the marker reference position in the first image of the still image.

In the X-ray imaging apparatus according to the first aspect of the present invention, preferably, the apparatus further includes an operation reception unit configured to accept an input operation from an operator, and is configured to set the marker reference position based on the input operation specifying a position on the first X-ray image displayed on the display unit. With this configuration, the operator's desired position on the first X-ray image can be set as the marker reference position while allowing the operator (surgeon) to visually recognize the first X-ray image.

In the X-ray imaging apparatus according to the first aspect of the present invention, preferably, the image processing unit is configured to generate the second image in which a plurality of virtual marker images are superimposed on the second X-ray image and calculate distances among the plurality of virtual marker images. With this configuration, it becomes unnecessary for an operator (surgeon) to measure the distance using a ruler, which can reduce the work burden of the operator (surgeon).

In this case, preferably, it is configured to display an image indicating the distances among the plurality of virtual marker images on the display unit together with the second image. With such a configuration, it becomes possible to allow an operator (surgeon) to visually recognize an image indicating the distances among the plurality of virtual marker images.

In the X-ray imaging apparatus configured to calculate the distances among the plurality of virtual marker images, preferably, the image processing unit is configured to acquire magnification ratio information of the second X-ray image and calculate distances in an actual scale among the plurality of virtual marker images based on the magnification ratio information. With such a configuration, even in the case of acquiring the distances in the actual scale, it is not necessary to perform the operation of measuring the distance using a real ruler, so that the work burden of the operator (surgeon) can be reduced.

An X-ray image display method according to a second aspect of the present invention is an X-ray image display method configured to capture an X-ray image by irradiating X-rays to a subject and detecting the X-rays that have passed through the subject, process the captured X-ray image, and display the X-ray image, the method comprising: acquiring a first image which is a first X-ray image in which a marker reference position is set; acquiring a second X-ray image captured separately from the first X-ray image and having a relative position between the subject and an imaging unit different from the first X-ray image; generating a second image in which a virtual marker image is superimposed at a corresponding position in the second X-ray image reflecting a change of the relative position from the marker reference position with respect to the second X-ray image; and displaying the second image.

In the X-ray image display method according to the second aspect of the present invention, by configuring as described above, even in cases where one of the imaging unit and the subject (region-of-interest) moves with respect to the other, it is possible to provide an X-ray image display method capable of allowing an operator to visually recognize a correct position of a region-of-interest in a subject using a virtual marker image.

In the X-ray image display method according to the second aspect of the present invention, preferably, the processing the X-ray image includes performing image processing of superimposing a virtual marker image at the marker reference position in the first image with respect to the first image. With this configuration, it is possible to allow an operator to visually recognize the marker reference position in the first image by the virtual marker image displayed on the first image.

BRIEF DESCRIPTION OF THE DRAWINGS

FIG. 19A is a diagram for explaining the processing (first image) in an X-ray imaging apparatus according to a third modification of the first and second embodiments of the present invention.

FIG. 19B is a diagram for explaining the processing (second image) in an X-ray imaging apparatus according to a third modification of the first and second embodiments of the present invention.

DESCRIPTION OF PREFERRED EMBODIMENTS

Hereinafter, embodiments embodying the present invention will be described with reference to the attached drawings.

First Embodiment (Configuration of X-Ray Imaging Apparatus)

First, the configuration of the X-ray imaging apparatus 100 according to a first embodiment of the present invention will be described with reference to FIG. 1 to FIG. 8.

The X-ray imaging apparatus 100 according to the first embodiment is configured, for example, as an angiography apparatus for capturing an image of a lower limb (leg) portion of a subject P (see FIG. 2) in a state in which a contrast agent is injected into a blood vessel. Here, the subject P is a living body, such as, e.g., a human body. When a surgeon (operator) measures the position and the length of the region-of-interest (affected part) in the lower limb of the subject P, in the X-ray imaging apparatus 100, a contrast agent is injected into the blood vessel of the lower limb of the subject P by a catheter (not shown), and an X-ray image (stitched image to be described later) is acquired.

For example, the indwelling position and the stent length of the stent to be placed in the affected part is determined by a surgeon who visually recognizes the stitched image. Thereafter, in the X-ray imaging apparatus 100, an X-ray image (a fluoroscopic image which will be described later) reflecting the vicinity of the affected part of the subject in a state in which no contrast agent exists is captured. Then, the surgeon who visually recognizes the fluoroscopic image carries out the medical treatment to the affected part and confirms, e.g., the indwelling position of the placed stent. Further, in the X-ray imaging apparatus 100, in some cases, the state of the affected part may be confirmed by a surgeon by reading and displaying the X-ray image captured in the past.

Figure 1:
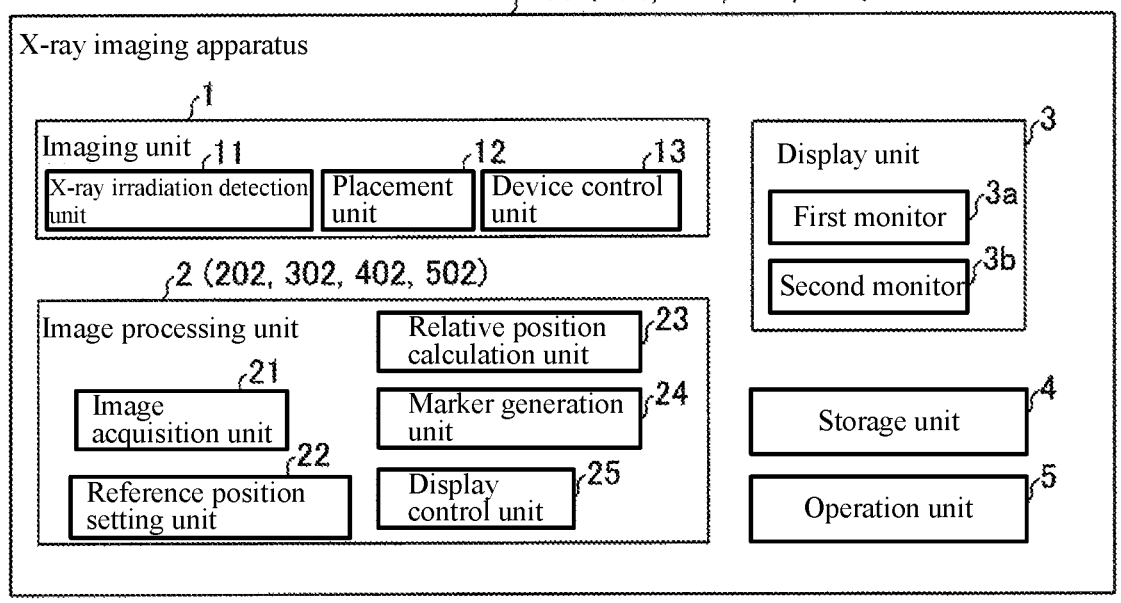
FIG. 1 is a block diagram showing an overall structure of an X-ray imaging apparatus according to first and second embodiments of the present invention.
Figure 2:
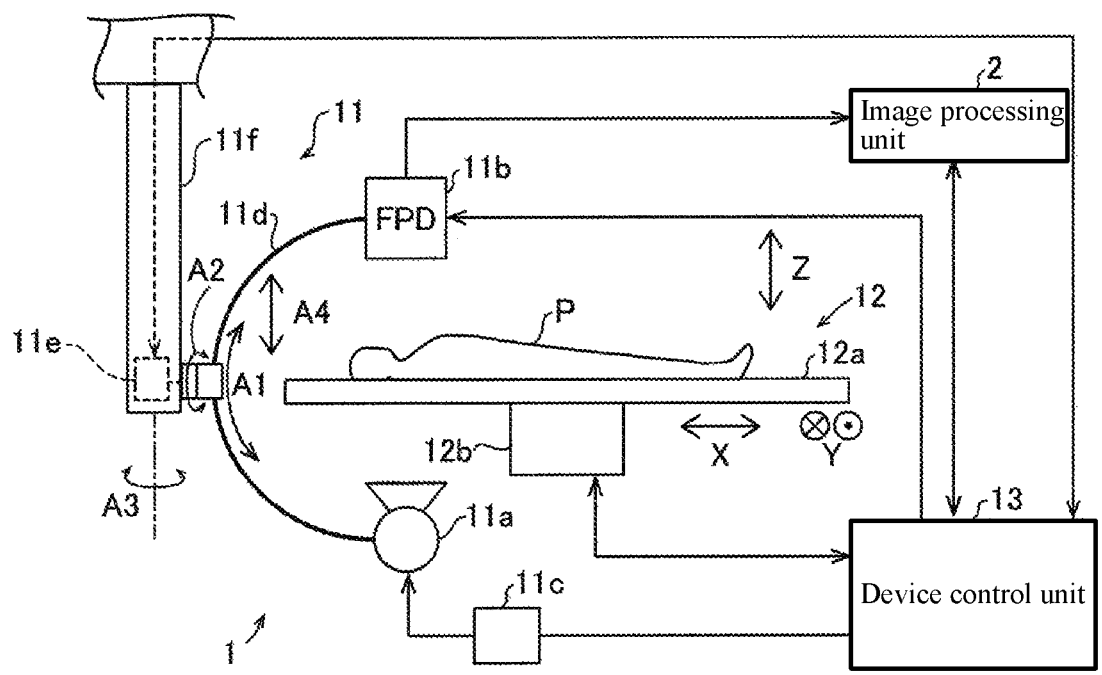
FIG. 2 is a schematic diagram showing a configuration of an imaging unit of the X-ray imaging apparatus according to the first embodiment of the present invention.

As shown in FIG. 1, the X-ray imaging apparatus 100 is equipped with an imaging unit 1, an image processing unit 2, a display unit 3, a storage unit 4, and an operation unit 5. As shown in FIG. 2, the imaging unit 1 is configured to irradiate X-rays to the subject P and detect the X-rays that have passed through the subject P to capture an X-ray image. The image processing unit 2 is configured to perform image processing of an X-ray image captured by the imaging unit 1. Note that the operation unit 5 is an example of the "operation reception unit" recited in claims.

The display unit 3 is configured as, for example, a liquid crystal display monitor. The display unit 3 is configured to display the X-ray image output from the image processing unit 2 or to display the X-ray image read from the storage unit 4. Further, the display unit 3 includes, for example, a plurality of monitors. For example, the display unit 3 includes a first monitor 3a and a second monitor 3b. For example, the first monitor 3a is used as a reference monitor for an operator (surgeon) to refer to an image. The second monitor 3b is used as a collection monitor for displaying sequentially collected images.

The storage unit 4 includes, for example, a nonvolatile memory. In the storage unit 4, programs to be used at the time of the processing of the image processing unit 2 and the device control unit 13 are stored, and the storage unit is configured to store captured X-ray images.

The operation unit 5 includes, for example, a mouse and a keyboard. The operation unit 5 is configured to accept an input operation from an operator (surgeon). The operation unit 5 is configured to transmit the accepted input operation to the image processing unit 2 and the device control unit 13.

(Configuration of Imaging Unit)

As shown in FIG. 2, the imaging unit 1 includes an X-ray irradiation detection unit 11, a placement unit 12, and a device control unit 13. Here, in the first embodiment, the X-ray irradiation detection unit 11 is configured to be movable with respect to the placement unit 12. Further, the placement unit 12 is configured to be movable with respect to the X-ray irradiation detection unit 11.

More specifically, the X-ray irradiation detection unit 11 includes an X-ray tube 11a, an FPD (flat panel detector) 11b, and an X-ray tube drive unit 11c. The X-ray irradiation detection unit 11 includes a C-shaped holder 11d for supporting the X-ray tube 11a and the FPD 11b and for moving the X-ray tube 11a and the FPD 11b and an arm drive unit 11e for moving the holder 11d based on the instruction from the device control unit 13.

The X-ray tube 11a is attached to one end portion of the holder 11d and is arranged on one side (lower side in FIG. 2) of the top board 12a of the placement unit 12. The X-ray tube 11a is configured to irradiate X-rays toward the subject P (FPD 11b) when a voltage is applied by the X-ray tube drive unit 11c.

The FPD 11b is attached to the other end portion of the holder 11d at the position facing the X-ray tube 11a. The FPD 11b is configured to detect the X-rays that have passed through the subject P and capture an X-ray image. The FPD 11b is connected to the image processing unit 2, and is configured to transmit the acquired X-ray image to the image processing unit 2.

The holder 11d is suspended, for example, from the ceiling of the room in which the X-ray imaging apparatus 100 is disposed by the support unit 11f. The arm drive unit 11e includes, for example, a motor, and is configured to move the holder 11d with respect to the top board 12a of the placement unit 12 by operating the motor based on the command from the device control unit 13.

For example, the arm drive unit 11e is configured so that the C-shaped holder 11d can be slidably moved along the direction of the arrow A1 and that the holder 11d can be rotatably moved along the direction of the arrow A2 and the direction of the arrow A3 centering the predetermined rotation axis, and the holder 11d can be moved vertically in the direction of the arrow A4. The arm drive unit 11e includes a position information detection unit (for example, encoder) and is configured to acquire position information (posture information and coordinate information) of the holder 11d (X-ray irradiation detection unit 11). The arm drive unit 11e is configured to transmit the obtained position information of the holder 11d to the device control unit 13.

The placement unit 12 includes a top board 12a configured to be able to place a subject P and a top board drive unit 12b for driving the top board 12a. The top board 12a is provided with a flat surface (placement surface) so that a subject P can be placed in a recumbent position. When the subject P is X-ray imaged, the subject P is fixed to the top board 12a, and the subject P moves together with the top board 12a. The top board drive unit 12b includes, for example, a motor, etc., and is configured to move the top board 12a in the horizontal direction (X-direction and Y-direction) and the vertical direction (Z-direction) by operating the motor based on the command from the device control unit 13.

The top board drive unit 12b is provided with a position information detection unit (for example, encoder). The top board drive unit 12b is configured to acquire the position information (coordinate information) of the top board 12a (placement unit 12) and transmit the acquired position information of the top board 12a to the device control unit 13. In this first embodiment, since the subject P moves integrally with the top board 12a, the position information of the region-of-interest of the subject P can be acquired (calculated) from the position information of the top board 12a.

The device control unit 13 includes, for example, a CPU (Central Processing Unit) and is configured to transmit the control signal (command) to the X-ray irradiation detection unit 11 and the placement unit 12. Further, the device control unit 13 is configured to acquire the information on the input operation accepted from the operator from the operation unit 5. Then, the device control unit 13 is configured to transmit the control signal to realize the arrangement relation (relative position) of the X-ray irradiation detection unit 11 and the placement unit 12 for imaging the desired portion of the subject P based on the information on the acquired input operation, the position information of the X-ray irradiation detection unit 11 (holder 11d), and the position information of the placement unit 12 (top board 12a).

In addition, the device control unit 13 is configured to acquire the magnification ratio information based on the position information of the X-ray irradiation detection unit 11 and the position information of the placement unit 12. The magnification ratio information includes, for example, the information on the ratio of the distance between the FPD 11b and the subject P (top board 12a) to the distance between the X-ray tube 11a and the FPD 11b and the information on the opening state of the collimator (X-ray diaphragm device) attached to the X-ray tube 11a. The device control unit 13 is configured to transmit the position information of the X-ray irradiation detection unit 11, the position information of the placement unit 12, and the magnification ratio information to the image processing unit 2. That is, the device control unit 13 is configured to transmit the information for acquiring the change of the relative position between the imaging unit 1 and the subject P (region-of-interest) to the image processing unit 2.

(Configuration of Image Processing Unit)

The image processing unit 2 includes an image processing circuit for performing the processing of an X-ray image. As shown as a functional block of the image processing circuit in FIG. 1, the image processing unit 2 includes an image acquisition unit 21, a reference position setting unit 22, a relative position calculation unit 23, a marker generation unit 24, and a display control unit 25. It should be noted that in FIG. 1, the configuration of the image processing unit 2 is illustrated as a functional block, but each unit may be configured as an individual hardware (circuit) for each function.

Here, in the first embodiment, the image processing unit 2 is configured to acquire a stitched image F1 (see FIG. 5) in which marker reference positions C1 to C6 are set with respect to the stitched image E1 (see FIG. 4) and generate a fluoroscopic image F2 (see FIG. 7) in which a virtual marker image H11 and virtual ruler images H12 and H13 are superimposed at corresponding positions C11 to C16 (see FIG. 6) in the fluoroscopic image E2 reflecting the change of the relative position from the marker reference positions C1 to C6 with respect to the fluoroscopic image E2 (see FIG. 6) captured separately from the stitched image E1 and different in the relative position between the subject P and the imaging unit 1 from the stitched image E1. The image processing unit 2 is configured to display the fluoroscopic image F2 on the display unit 3 (second monitor 3b). Note that the stitched image E1 is an example of the "first X-ray image" recited in claims. Further note that the stitched image F1 is an example of the "first image" recited in claims. Further note that the fluoroscopic image E2 is an example of the "second X-ray image" recited in claims. Further note that the fluoroscopic image F2 is an example of the "second image" recited in claims. Hereinafter, the detail description will be made.

The image acquisition unit 21 has a function of acquiring an X-ray image from the imaging unit 1 and generating a stitched image E1 and a fluoroscopic image E2. It should be noted that in the specification of this application, the "stitched image" is described to mean an image constituted by connecting images captured at each of a plurality of relative positions (relative position between the X-ray irradiation detection unit 11 and the top board 12a). Further note that the "fluoroscopic image" means an image captured in one relative position. In the following description, when simply described as a "relative position", it is described as meaning the relative position between the X-ray irradiation detection unit 11 and the placement unit 12 (subject P).

Figure 3:
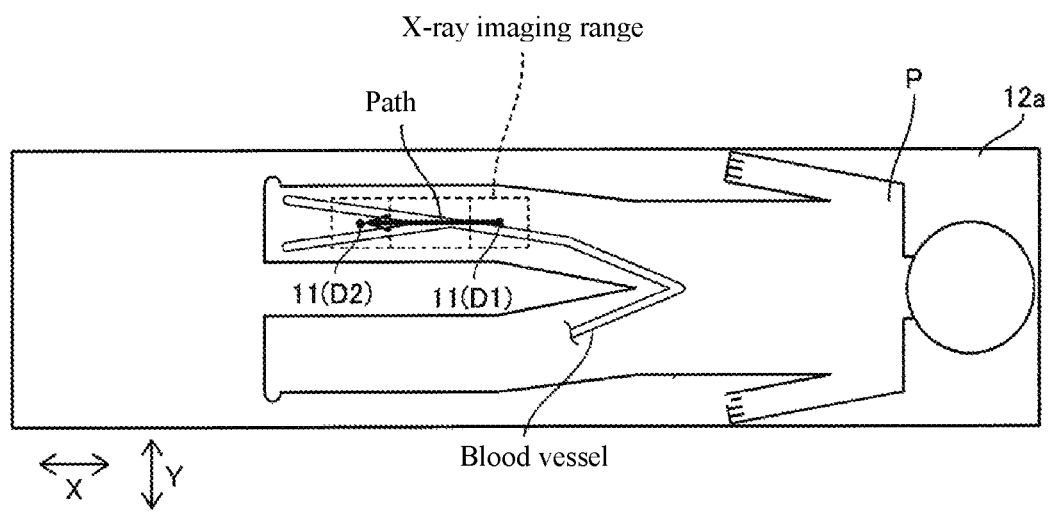
FIG. 3 is a diagram for explaining capturing of a stitched image in the X-ray imaging apparatus according to the first embodiment of the present invention.

Specifically, in the first embodiment, as shown in FIG. 3 and FIG. 4, the X-ray imaging apparatus 100 is configured to perform X-ray imaging at a plurality of relative positions of the X-ray irradiation detection unit 11 and the placement unit 12 (subject P) (from the point D1 to the point D2 in FIG. 3). Specifically, the X-ray imaging apparatus 100 is configured to perform X-ray imaging while relatively moving the X-ray irradiation detection unit 11 and the top board 12a along the path previously stored in the storage unit 4 or the path based on the input operation input to the operation unit 5. The point D1 and the point D2 each are the center position (position of the center of gravity) of the FPD 11b as viewed from the X-ray tube 11a.

Figure 4A:
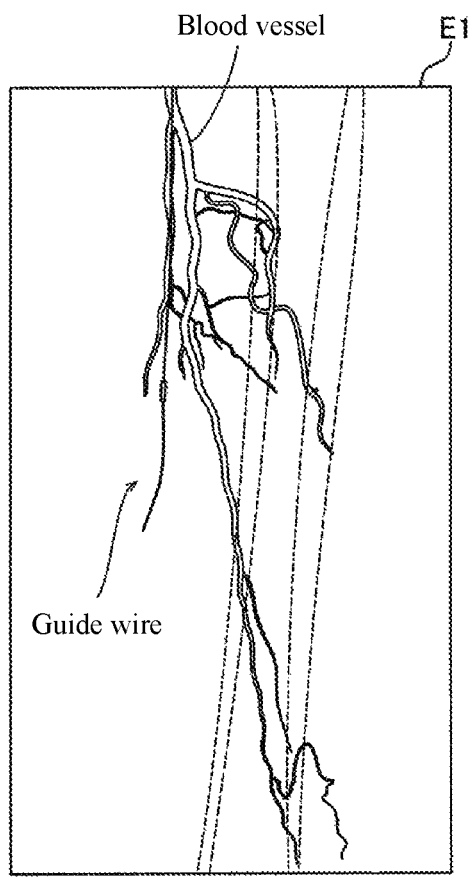
FIG. 4A is a diagram for explaining displaying of the stitched image in the X-ray imaging apparatus according to the first embodiment of the present invention.

Specifically, in FIG. 3, an example is shown in which an X-ray image is sequentially captured from the thigh side (point D1) to the lower leg side (point D2) of the lower limb of the subject P while moving the X-ray irradiation detection unit 11 with respect to the subject P. Then, the image acquisition unit 21 of the image processing unit 2 performs image processing in which a plurality of captured X-ray images are joined, so that the stitched image E1 as shown in FIG. 4A is acquired.

FIG. 4 shows an angiographic image of the lower limb portion of the subject P. That is, in the first embodiment, the stitched image E1 is an X-ray image including the image of the contrast agent injected into the subject P. In detail, the stitched image E1 includes an image in which a part of the X-ray image captured as a moving image while changing the relative position during contrasting a contrast agent injected into the blood vessel of the subject P as a still image. That is, the stitched image E1 is acquired as a last image hold. As a result, the X-ray imaging apparatus 100 is configured to display the angiogrammed stitched image E1 in the display unit 3 (the first monitor 3a) even after the contrast agent has flowed away from the blood vessel in the vicinity of the region-of-interest of the subject P to another part.

Figure 4B:
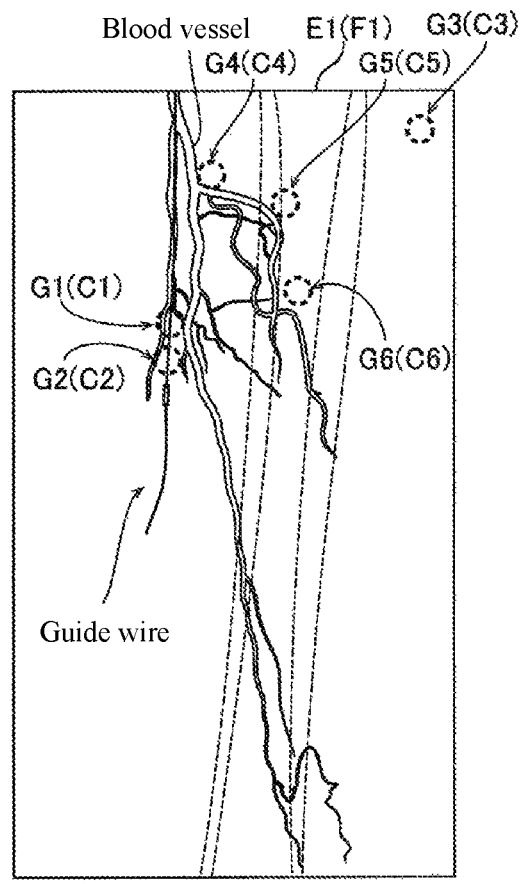
FIG. 4B is a diagram for explaining setting displaying of a marker reference position in the stitched image in the X-ray imaging apparatus according to the first embodiment of the present invention.

As shown in FIG. 4B, the reference position setting unit 22 has a function of setting marker reference positions C1 to C6 with respect to the stitched image E1. It should be noted that the "marker reference position" is a reference position for generating a virtual marker image and a virtual ruler image, which will be described later, and can be set outside the positions of the marker reference positions C1 to C6 shown in FIG. 4B.

Specifically, as shown in FIG. 4B, in the first embodiment, the reference position setting unit 22 is configured to set the marker reference positions C1 to C6 based on the input operation by the operator (surgeon) specifying the positions on the stitched image E1 displayed on the display unit 3. Specifically, when an operation to specify specified positions G1 to G6 on the angiography stitched image E1 displayed on the display unit 3 is performed to the operation unit 5 by an operator (surgeon), the reference position setting unit 22 is configured to obtain the information of this input operation from the operation unit 5 and set the positions (matching positions) corresponding to the specified positions G1 to G6 as marker reference positions C1 to C6. Note that the "specified position" means a coordinate position on the image selected by the operator, and may be arbitrarily set at positions other than the specified positions G1 to G6 shown in FIG. 4B.

Here, setting of the marker reference positions C1 to C6 is carried out, for example, when determining the indwelling position of the stent, the length of the stent, etc. (determining the region-of-interest) after the operator placed the guide wire in the blood vessel at the lower limb portion of the subject P.

The input operation includes a setting operation of a display position of a pair of virtual marker images, a setting operation of a display position of a virtual ruler image, a storage instruction operation of a scale value of a virtual ruler image, a highlighting operation of a scale value of a virtual ruler image, an operation of clearing the displaying of a pair of virtual marker images or a virtual ruler image, and an operation of cancelling a highlight display of a scale value of a virtual ruler image. The reference position setting unit 22 has a function of performing the setting processing of the marker reference positions according to the input operation.

Figure 5:
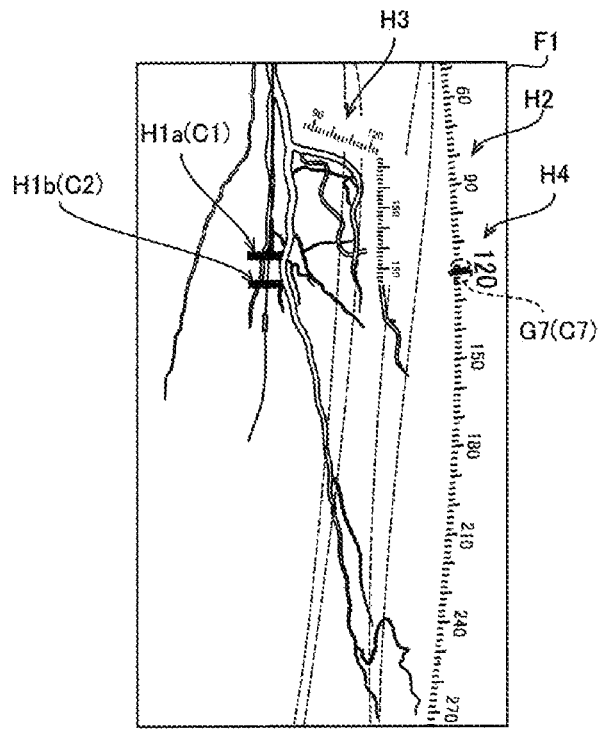
FIG. 5 is a diagram for explaining a virtual marker image superimposed on the stitched image in the X-ray imaging apparatus according to the first embodiment of the present invention.

For example, when the setting operation of the display position of a pair of virtual marker images is performed at the specified position G1 and G2, the reference position setting unit 22 sets marker reference positions C1 and C2 with the specified positions G1 and G2 defined as the display reference positions of a pair of virtual marker images H1a and H1b (see FIG. 5). Further, when the setting operation of the display position of the virtual ruler image is performed on a specified position G3, the reference position setting unit 22 sets the marker reference position C3 as the display reference position of the virtual ruler image H2 (see FIG. 5) arranged along the longitudinal direction of the stitched image E1 and the reference position of the corresponding position which will be described later.

For example, when the setting operation of the display position of the virtual ruler image is performed for the three specified positions G4 to G6, the reference position setting unit 22 sets three specified positions G4 to G6 as marker reference positions C4 to C6 which are reference positions for displaying a virtual ruler image H3 (see FIG. 5) having a bent shape and reference positions of corresponding positions which will be described later.

The marker generation unit 24 has a function of generating a virtual marker image and a virtual ruler image to be displayed on a marker reference position or a corresponding position to be described later. Further, the display control unit 25 has a function of displaying (outputting) the image processed X-ray image on the display unit 3. Here, the "virtual marker image" is an image to be displayed in a manner as to be further superimposed on the captured X-ray image, and an image to be displayed by a display method (a mark such as, e.g., a white mark and a black mark) visible in the X-ray image. In addition, the "virtual ruler image" is an image including at least a scale image among the scale image and an image showing scale values (numbers). For example, in the first embodiment, a virtual marker image and a virtual ruler image are stored in advance in the storage unit 4, and the virtual marker image and the virtual ruler image are read out from the storage unit 4 by the marker generation unit 24 and displayed on the corresponding position.

For example, as shown in FIG. 5, in the first embodiment, the marker generation unit 24 performs image processing of superimposing a pair of virtual marker images H1a and H1b at the positions of the marker reference positions C1 and C2 set by the reference position setting unit 22 with respect to the stitched image E1 (see FIG. 4). Further, the marker generation unit 24 performs image processing of superimposing a virtual ruler image H2 extending along the longitudinal direction of the stitched image E1 at the marker reference position C3. Further, the marker generation unit 24 performs image processing of superimposing a virtual ruler image H3 having a bent shape corresponding to the shape of the blood vessel at the marker reference positions C4 to C6.

Then, the display control unit 25 is configured to perform control to cause the display unit 3 (first monitor 3a) to display the stitched image F1 in which the virtual marker images H1a and H1b and the virtual ruler images H2 and H3 are superimposed by the marker generation unit 24.

Specifically, as shown in FIG. 5, the pair of virtual marker images H1a and H1b and the virtual ruler images H2 and H3 are displayed on the stitched image F1 in a manner as to be visually recognized by an operator by a display method distinguishable from the structural objects (blood vessels and bones) of the subject P and indwelling objects (catheter, stent, balloon, etc.). For example, the pair of virtual marker images H1a and H1b has a rectangular shape (or circular shape) of, e.g., white and black, and is configured as a mark to be displayed as two marks (a pair of marks) with a predetermined distance therebetween. For example, the pair of virtual marker images H1a and H1b can indicate arrangement scheduled positions of a stent and both end portions of a balloon.

Further, the virtual ruler image H2 and the virtual ruler image H3 each include a scale image and an image of scale values (numbers) for each predetermined scale. Although the virtual ruler image H2 is shown in an arc shape with respect to the longitudinal direction of the stitched image F1 in FIG. 5, the virtual ruler image H2 may be linearly generated and arranged in parallel with the longitudinal direction of the stitched image F1. Further, the virtual ruler image H2 may be displayed so as to be arranged not only in the longitudinal direction but also in an arbitrary direction (for example, a direction having a predetermined inclination angle in the lateral direction or the longitudinal direction).

In addition, the marker generation unit 24 is configured to set the magnitudes of the scale images of the virtual ruler images H2 and H3 based on the magnification ratio information and generate the image of the scale value as a value substantially matching the distance value of the actual scale. In FIG. 5, an example is shown in which the virtual ruler image H3 is superimposed and displayed so as to fill the background image of the virtual ruler image H3. However, the image processing unit 2 may be configured to display the virtual ruler image H3 (for example, translucent virtual ruler image) while displaying the angiogram stitched image E1 positioned on the background of the position of the virtual ruler image H3.

With the virtual ruler image H2, the scale value (for example "120") of the region-of-interest (pair of virtual marker images H1a and H1b) becomes visible. Then, when the operation unit 5 accepts a highlighting operation (specified position G7) of the scale value of the virtual ruler image, the reference position setting unit 22 sets the specified position G7 as the marker reference position C7.

Then, as shown in FIG. 5, the marker generation unit 24 performs image processing to enlarge the display size of the scale and the scale value of the corresponding marker reference position C7 in the virtual ruler image H2 (for example, the display of "120"). Then, the image processing unit 2 performs control to store the information on the stitched image F1, the marker reference positions C1 to C7, and the highlight displayed scale value in the storage unit 4. Note that the "highlight display" includes, for example, displaying an image with a larger size than other scale value images and displaying an image by changing the color with respect to other scale value images. Also, the storing of the scale value information is not limited to storing of one scale value, but may be storing of a plurality of scale values.

Also, the display control unit 25 is configured to erase the display of the pair of virtual marker images H1a and H1b or erase the display of the virtual ruler images H2 and H3 when the display erase operation of the pair of virtual marker images or the virtual ruler images is inputted. Further, the display control unit 25 is configured to perform image processing of canceling (restoring) the highlighting H14 when an abort operation of highlighting the scale value of the virtual ruler image is input.

Figure 6:
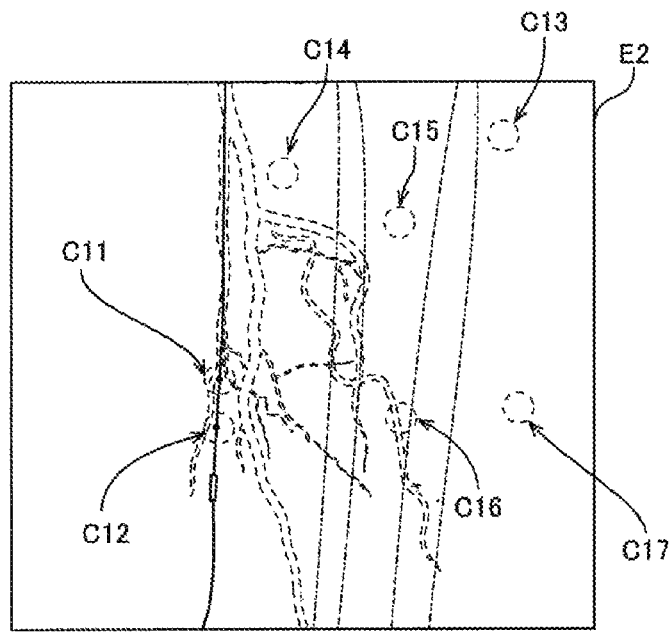
FIG. 6 is a diagram for explaining the acquisition of the corresponding position of a fluoroscopic image in the X-ray imaging apparatus according to the first embodiment of the present invention.

After the marker reference positions C1 to C7 (region-of-interest) are set, in the X-ray imaging apparatus 100, a fluoroscopic image E2 captured at one relative position is acquired separately from the stitched image E1. In detail, the X-ray imaging apparatus 100 acquires the fluoroscopic image E2 in a state in which the X-ray dose is reduced in comparison with the case of capturing the stitched image E1. In the X-ray imaging apparatus 100, while displaying the fluoroscopic image E2 on the display unit 3 (second monitor 3b) in real time as a moving image, the fluoroscopic image E2 is kept being acquired while moving the X-ray irradiation detection unit 11 or the top board 12a based on the input operation by an operator. At this time, for example, no contrast agent is injected into the subject P, and as shown in FIG. 6, the blood vessel is not clearly reflected on the fluoroscopic image E2. Note that in FIG. 6, the blood vessels are indicated by dotted lines for convenience of explanation.

The relative position calculation unit 23 has a function of acquiring (calculating) the information on the change of the relative position between the imaging unit 1 and the subject P and setting the corresponding position. Here, the "corresponding position" means the corresponding position in the fluoroscopic image F2 reflecting the change of the relative position between the imaging unit 1 and the subject P with respect to the marker reference position in the stitched image F1.

Specifically, as shown in FIG. 6, in the first embodiment, the relative position calculation unit 23 is configured to acquire (calculate) the information on the change of the relative position based on the movement information of the X-ray irradiation detection unit 11, the movement information and the magnification ratio information of the placement unit 12. That is, the relative position calculation unit 23 is configured to calculate position information for matching the position of the fluoroscopic image E2 with the imaging region of the stitched image F1. Then, the relative position calculation unit 23 is configured to set the corresponding positions C11 to C17 in the fluoroscopic image E2 based on the acquired information on the change of the relative position.

Figure 7:
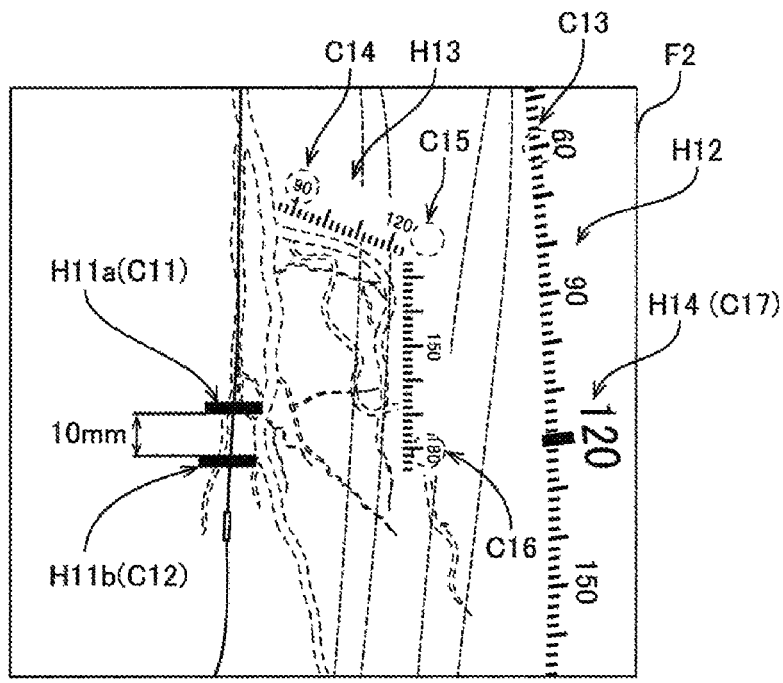
FIG. 7 is a diagram for explaining the virtual marker image superimposed on the fluoroscopic image in the X-ray imaging apparatus according to the first embodiment of the present invention.

In the first embodiment, as shown in FIG. 7, the marker generation unit 24 is configured to generate the fluoroscopic image F2 in which the virtual marker images H11a and H11b and the virtual ruler images H12 and H13 at the corresponding positions C11 to C17 in the fluoroscopic image E2 reflecting the change of the relative position between the imaging unit 1 and the subject P from the marker reference positions C1 to C7 with respect to the fluoroscopic image E2.

In detail, the marker generation unit 24 performs image processing of superimposing a pair of virtual marker images H11a and H11b at the corresponding positions C11 and C12. In addition, the marker generation unit 24 performs image processing superimposing the virtual ruler image H12 extending in the longitudinal direction at the corresponding position C13. The marker generation unit 24 performs image processing of superimposing a bent virtual ruler image H13 at the corresponding position C14 to C16.

For example, when the position of the subject P in which the pair of virtual marker images H1a and H1b of the stitched image F1 are displayed is set as the indwelling scheduled position of the stent in the subject P, the pair of virtual marker images H11a and H11b displayed in the fluoroscopic image F2 are also displayed at substantially the same position as the indwelling scheduled position of the stent in the subject P. Further, the virtual ruler images H12 and H13 and the highlighting H4 are also displayed in a manner as to be superimposed at the positions of the virtual ruler images H2 and H3 displayed on the stitched image F1 and the subject P corresponding to (matching) the highlighting H4. Here, in the X-ray imaging apparatus 100, the fluoroscopic image F2 is displayed on the second monitor 3b in a state in which the stitched image F1 is displayed on the first monitor 3a. That is, the stitched image F1 and the fluoroscopic image F2 are simultaneously displayed on the display unit 3.

Figure 8:
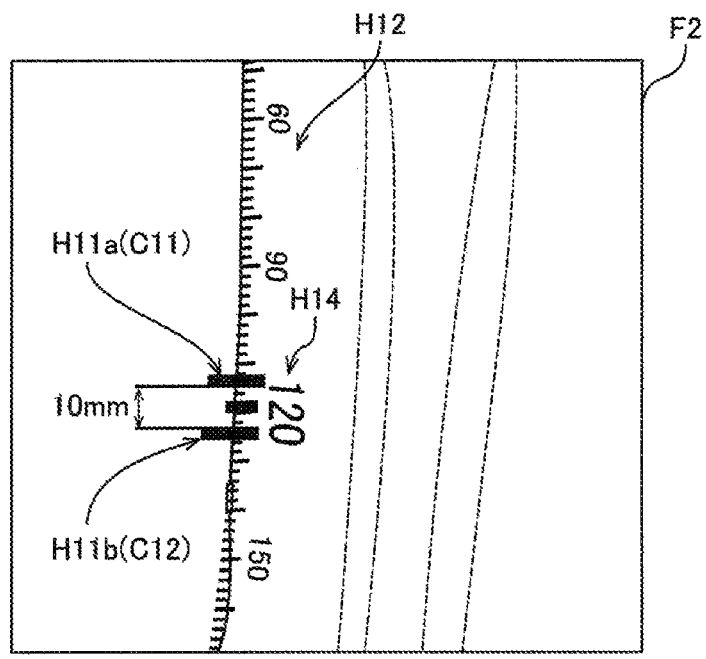
FIG. 8 is a diagram for explaining the movement processing of the virtual marker image superimposed on the fluoroscopic image in the X-ray imaging apparatus according to the first embodiment of the present invention.

As shown in FIG. 8, the marker generation unit 24 is configured to perform image processing of moving and displaying the virtual ruler image H13 and the highlighting H14 to the corresponding positions C11 and C12 which are positions corresponding to the region-of-interest based on the input operation from the operator. As a result, the image processing unit 2 can display the virtual ruler image H13 and the highlighting H14 in the vicinity of the pair of virtual marker images H11a and H11b (region-of-interest).

Further, the display control unit 25 of the image processing unit 2 is configured to calculate the distance value in the actual scale between the pair of virtual marker images H11a and H11b based on the magnification ratio information and control the display of the image showing the distance value (for example, "10 mm") in the actual scale between the pair of virtual marker images H11a and H11b together with the fluoroscopic image F2.

(X-ray Image Display Method)

Figure 9:
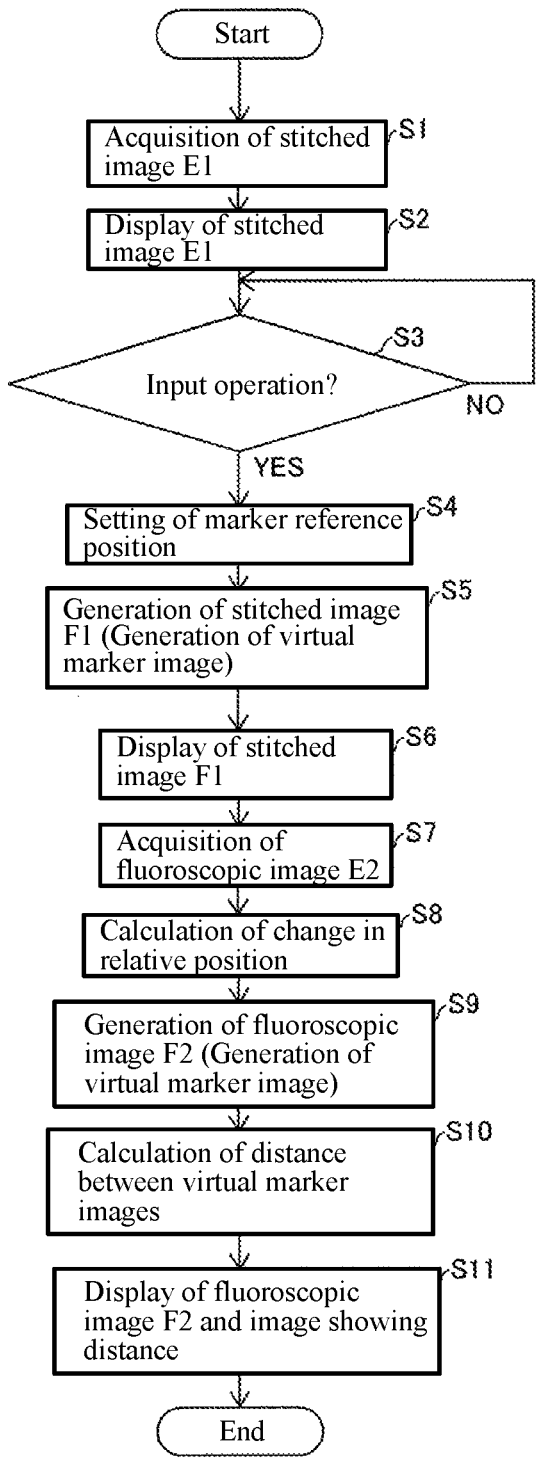
FIG. 9 is a flowchart for explaining the X-ray image display processing according to the first embodiment of the present invention.

Next, with reference to FIG. 9, an X-ray image display method (X-ray image display processing) by the first X-ray imaging apparatus 100 of the first embodiment will be described. The X-ray image display processing is executed by the image processing unit 2 and the device control unit 13.

Here, the X-ray image display method according to the first embodiment is a method that acquires the stitched image F1 which is the stitched image E1 in which the marker reference positions C1 to C6 are set, acquires the fluoroscopic image E2 captured separately from the stitched image E1 and different from the stitched image E1 in the relative position between the subject P and the imaging unit 1, generates the fluoroscopic image F2 in which a pair of virtual marker images H11a and H11b and virtual ruler images H12 and H13 are superimposed at the corresponding positions C11 to C16 in the fluoroscopic image E2 reflecting the change of the relative position from the marker reference positions C1 to C6 with reference to the fluoroscopic image E2, and display the fluoroscopic image F2.

Further, the X-ray image display method according to the first embodiment includes performing image processing of superimposing a pair of virtual marker images H1 and virtual ruler images H2 and H3 at the marker reference positions C1 to C6 with respect to the stitched image E1. That is, at the positions corresponding to the pair of virtual marker images H1a and H1b and the virtual ruler images H2 and H3 displayed in the stitched image F1, the display positions of the pair of virtual marker images H11a and H11b and the virtual ruler images H12 and H13 are made to be reflected (followed). Hereinafter, the X-ray image display method (X-ray image display processing) will be specifically described.

In Step S1, a stitched image E1 of the lower limb portion of the subject P in a state in which a contrast agent is injected is acquired. That is, while at least one of the X-ray irradiation detection unit 11 and the top board 12a is moved relative to the other, an X-ray image of the lower limb portion of the subject P is captured at the plurality of relative positions. Thereafter, the process proceeds to Step S2.

In Step S2, the stitched image E1 is displayed on the display unit 3. Specifically, the stitched image E1 as a still image (last image hold) at the time when the contrast agent in the moving image substantially fills the blood vessel is displayed on the display unit 3 (first monitor 3a). Thereafter, the process proceeds to Step S3.

In Step S3, it is determined whether or not the operation unit 5 has accepted an input operation. This determination is repeated until an input operation is accepted, and when an input operation is accepted, the process proceeds to Step S4.

In Step S4, marker reference positions C1 to C6 are set based on the input operation. Specifically, as shown in FIG. 4B, positions matching the specified positions G1 to G6 are set as marker reference positions C1 to C6, thereafter, the process proceeds to Step S5.

In Step S5, image processing of superimposing the pair of virtual marker images H1a and H1b and the virtual ruler images H2 and H3 at the marker reference positions C1 to C6 with respect to the stitched image E1 is performed to generate the stitched image F1. At this time, as shown in FIG. 5, the highlighting H4 may be displayed based on the input operation in Step S4. Thereafter, the process proceeds to Step S6.

In Step S6, the stitched image F1 is displayed on the display unit 3. Thereafter, the process proceeds to Step S7. In Step S7, the fluoroscopic image E2 for displaying an image of one relative position as a moving image is acquired. Thereafter, the process proceeds to Step S8. Then, in Step S8, the change of the relative position is calculated based on at least one of the position information of the X-ray irradiation detection unit 11 and the position information of the placement unit 12. Thereafter, the process proceeds to Step S9.

In Step S9, the fluoroscopic image F2 in which the pair of virtual marker images H11a and H11b and the virtual ruler images H12 and H13 are superimposed at the corresponding positions C11 to C16 in the fluoroscopic image E2 reflecting the change of the relative position is generated. Thereafter, the process proceeds to Step S10.

In Step S10, the distance between the pair of virtual marker images H11a and H11b is calculated. Thereafter, the process proceeds to Step S11. In Step S11, the fluoroscopic image F2 and the image showing the distance value between the pair of virtual marker images H11a and H11b are displayed on the display unit 3. For example, in the first embodiment, the stitched image F1 in which the pair of virtual marker images H1a and H1b are superimposed in Step S6 is displayed on the first monitor 3a of the display unit 3, in the state in which the stitched image F1 displayed on the first monitor 3a, the fluoroscopic image F2 in which the pair of virtual marker images H11a and H11b are superimposed in Step S10 is displayed on the second monitor 3b of the display unit 3. That is, the stitched image F1 and the fluoroscopic image F2 are displayed simultaneously. After that, the X-ray image display processing (X-ray image display method) by the first embodiment is terminated.

Effects of First Embodiment

In the first Embodiment, the following effects can be obtained.

In the first embodiment, as described above, the image processing unit 2 is configured to acquire the stitched image F1 in which the marker reference positions C1 to C6 is set in the stitched image E1, and generate the fluoroscopic image F2 in which the pair of virtual marker images H11a and H11b and the virtual ruler images H12 and H13 (hereinafter referred to as "virtual marker image, etc.") are superimposed at the corresponding positions C11 to C16 in the fluoroscopic image E2 reflecting the change of the relative position from the marker reference positions C1 to C6 with respect to the fluoroscopic image E2 captured separately from the stitched image E1 and having a relative position different from that of the stitched image E1 between the subject P and the imaging unit 1. With this, even in cases where the position of the region-of-interest in the X-ray image at the time of capturing the stitched image E1 is different from the position of the region-of-interest of the X-ray image at the time of capturing the fluoroscopic image E2, it is possible to appropriately display a virtual marker image or the like at the corresponding position C11 to C16 (the position of the position-of-interest) in the fluoroscopic image F2. As a result, even when one of the imaging unit 1 and the subject P (region-of-interest) moves relative to the other, by using the virtual marker image, etc., it is possible to allow the operator to visually recognize the exact position of the region-of-interest in the subject P. As a result, by performing imaging in a state in which the contrast agent is injected at the position of the region-of-interest of the subject P at the time of capturing the stitched image E1, at the time of capturing the fluoroscopic image E2, it is possible to allow the operator to visually recognize the exact position of the region-of-interest in the subject P with the virtual marker image, etc., without injecting a contrast agent again. Therefore, the usage of the contrast agent can be reduced.

In the first embodiment, as described above, the image processing unit 2 is configured to generate the pair of virtual marker images H11a and H11b. As a result, unlike the virtual marker image showing one point, it is possible to visually recognize the distance between the pair of virtual marker images H11a and H11b.

Further, in the first embodiment, as described above, the image processing unit 2 is configured to generate the virtual ruler images H12 and H13. This allows the operator to visually recognize the magnitude of the distance on the fluoroscopic image F2 using the virtual ruler images H12 and H13. Further, as shown in FIG. 8, when the virtual ruler image H12 is displayed along the shape of the blood vessel, even in cases where the blood vessel is not imaged in the fluoroscopic image F2, it is possible for the operator to visually recognize the shape of the blood vessel.

Further, in the first embodiment, as described above, the image processing unit 2 is configured to perform the image processing of superimposing a virtual marker image or the like at the marker reference positions C1 to C6 with respect to the stitched image F1. This allows the operator to visually recognize the marker reference positions C1 to C6 in the stitched image F1 by the virtual marker image displayed in the stitched image F1.

Further, in the first embodiment, as described above, the image processing unit 2 is configured to acquire the change of the relative position based on the movement information of at least one of the subject P and the imaging unit 1, and generate the fluoroscopic image F2 in which a virtual marker image and the like are superimposed at the corresponding positions C11 to C16 in the fluoroscopic image E2 reflecting the acquired relative position change. With this configuration, by acquiring the movement information of at least one of the subject P and the imaging unit 1, it is possible to easily acquire the change of the relative position between the subject P and the imaging unit 1.

Further, in the first embodiment, as described above, the imaging unit 1 is provided with an X-ray irradiation detection unit 11 for irradiating X-rays to the subject P and for detecting the X-rays that have passed through the subject P and a placement unit 12 capable of placing the subject P. Further, at least one of the X-ray irradiation detection unit 11 and the placement unit 12 is configured to be movable with respect to the other. The image processing unit 2 is configured to acquire the change of the relative position based on the movement information of at least one of the X-ray irradiation detection unit 11 and the placement unit 12. With this, by acquiring the movement information of at least one of the X-ray irradiation detection unit 11 and the placement unit 12, it is possible to acquire the information on the change of the position of the imaging unit 1 with respect to the subject P. As a result, for example, if the imaging location of the subject P is fixed to the placement unit 12 at the time of imaging, it is possible to acquire the change of the relative position between the subject P and the imaging unit 1 without acquiring the movement information of subject P. Therefore, it is possible to suppress the burden of processing in the image processing unit 2 from being increased.

Further, in the first embodiment, as described above, the image processing unit 2 is configured to acquire the stitched image F1 captured at a plurality of relative positions. With this, even in cases where the relative position between the stitched image F1 and the fluoroscopic image F2 is different, the virtual marker image or the like can be displayed at an appropriate position in the fluoroscopic image F2.

Further, in the first embodiment, as described above, the image processing unit 2 is configured to acquire the stitched image F1 and the fluoroscopic image F2 captured at one relative position. Here, in general, when X-ray imaging the lower limb portion of the subject P, initially, the stitched image E1 is X-ray imaged, and then the region-of-interest (such as the placement position of the stent) is determined by a surgeon while the stitched image E1 is being visually recognized by the surgeon. Thereafter, one (single) fluoroscopic image E2 is captured at one relative position, and the surgeon preforms a medical treatment of the region-of-interest. Considering this procedure, in the first embodiment, by configuring as described above, the marker reference positions C1 to C6 are set in the stitched image F1, and the virtual marker image and the like can be displaced at the proper position of the region-of-interest in a single fluoroscopic image F2. Therefore, the convenience for a surgeon (operator) can be improved.

Further, in the first embodiment, as described above, the stitched image F1 and the fluoroscopic image F2 are images reflecting the lower limb portion of the subject P. Here, a stitched image is generally generated when a lower limb portion of a subject P is X-ray imaged. Considering this point, in the first embodiment, by configuring as described above, even in cases where a stitched image of a lower limb portion is X-ray imaged, the region-of-interest can be visually recognized by a virtual marker image at an appropriate position.

Further, in the first embodiment, the fluoroscopic image F2 is a moving image as described above. With this, the operator (surgeon) can perform an operation (medical treatment) on the region-of-interest while visually recognizing the fluoroscopic image F2 as a moving image in which a virtual marker image and the like are superimposed and displayed.

Further, in the first embodiment, as described above, the stitched image F1 is an image including the image of the contrast agent injected into the subject P, and the fluoroscopic image F2 is an image not including the image of the contrast agent. Here, when X-ray imaging a subject P (living body), X-ray imaging is first performed in a state in which a contrast agent is injected, and the region-of-interest (stent placement position, etc.) is determined by a surgeon while the contrast image is being visually recognized by the surgeon. After that, a medical treatment is performed by a surgeon with respect to the subject P in a state in which no contrast agent exists. Considering this procedure, in the first embodiment, by configuring as described above, when a surgeon performs a medical treatment on a region-of-interest, a virtual marker image, etc., corresponding to the region-of-interest can be displayed appropriately in an image not including the image of the contrast agent.

In the first embodiment, as described above, the stitched image F1 includes an image (last image hold) in which a part of the image in the moving image is displayed as a still image. Here, for example, in the case of a moving image acquired in a state in which the contrast agent is injected into the subject P, there is a disadvantage that as the contrast agent flows out of the blood vessel in the imaging region, the contrast agent changes from the state in which the contrast agent is imaging the region-of-interest position to the state in which it is not imaging. In this respect, in the first embodiment, by configuring as described above, for example, it is possible to display it on the display unit 3 as a still image in a state in which the contrast agent contrasts the vicinity of the position which becomes a region-ofinterest. Therefore, the marker reference positions C1 to C6 can be easily set in the stitched image F1 of the still image.

Further, in the first embodiment, as described above, the X-ray imaging apparatus 100 is provided with an operation unit 5 for accepting an input operation from an operator. Further, the image processing unit 2 is configured so that marker reference positions C1 to C6 are set based on the input operation specifying the position on the stitched image E1 displayed on the display unit 3. With this, it is possible to set the position desired by the operator on the stitched image E1 (specified positions G1 to G6) as marker reference positions C1 to C6 while allowing the operator (surgeon) to visually recognizing the stitched image E1.

Further, in the first embodiment, as described above, the image processing unit 2 is configured to generate the fluoroscopic image F2 in which a plurality of virtual marker images (a pair of virtual marker images H11) is superposed on the fluoroscopic image E2 and calculate the distance between a plurality of virtual marker images. This eliminates the need to perform the operation of measuring the distance using a ruler by the operator (surgeon), so that the workload of the operator (surgeon) can be reduced.

Figure 14:
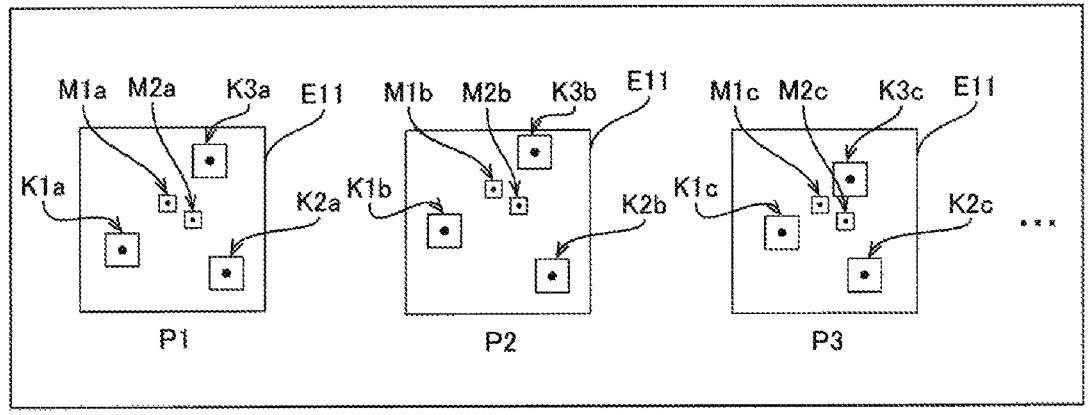
FIG. 14 is a diagram for explaining the acquisition of the movement information of the heartbeat feature points and the acquisition of the movement information of a pair of actual markers on the first X-ray image in the X-ray imaging apparatus according to the second embodiment of the present invention.

As shown in FIG. 14, the heartbeat feature points K1 to K3 and the pair of real markers M1 and M2 are objects moving in accordance with the heartbeat, and move while tracing the same trajectory for each heartbeat (period). Then, they return to the same positions on the X-ray image at every period of the heartbeat.

Further, in the first embodiment, as described above, the image processing unit 2 is configured to acquire the magnification ratio information of the fluoroscopic image E2 and calculate the distance in the actual scale between the plurality of virtual marker images based on the magnification ratio information. With this configuration, even in the case of acquiring the distance in the actual scale, it is not necessary to perform the operation of measuring the distance using a real ruler, so that the work burden of the operator (surgeon) can be reduced.

Second Embodiment

Next, with reference to FIG. 1 and FIG. 10 to FIG. 15, the configuration of the X-ray imaging apparatus 200 according to a second embodiment of the present invention will be described. In this second example, unlike the first embodiment configured to acquire the change of the relative position based on the position information of the X-ray irradiation detection unit 11 and the position information of the placement unit 12, it is configured to acquire the change of the relative position based on the movement information of the heartbeat feature points K1 to K3 in the subject P in the X-ray image. The same reference numerals are allotted to the same configurations as those of the first embodiment in the drawings, and the description thereof will be omitted.

The X-ray imaging apparatus 200 according to the second embodiment is configured to photograph (image) the heart part, etc., of the subject P. For example, in the X-ray imaging apparatus 200 according to the second embodiment, a guide wire is inserted via a catheter introduced in the blood vessel of the heart part of the subject P, and an X-ray image (first X-ray image) in a state in which a balloon is placed in the stenosed segment of the blood vessel is captured. Thereafter, the balloon is expanded to perform the medical treatment of the stenosis of the blood vessel, and after removing the balloon from the blood vessel, the X-ray image (second X-ray image) is captured.

Figure 10:
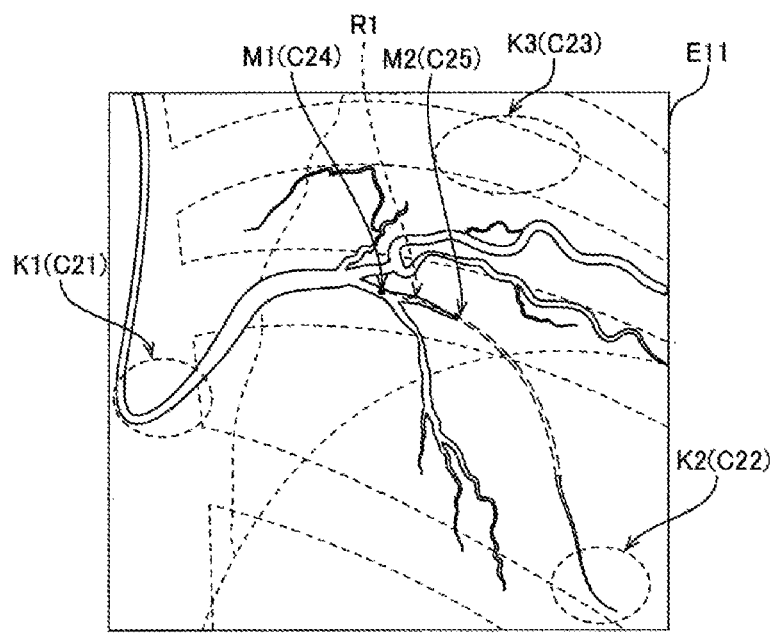
FIG. 10 is a diagram for explaining a first X-ray image in the X-ray imaging apparatus according to a second embodiment of the present invention.
Figure 11:
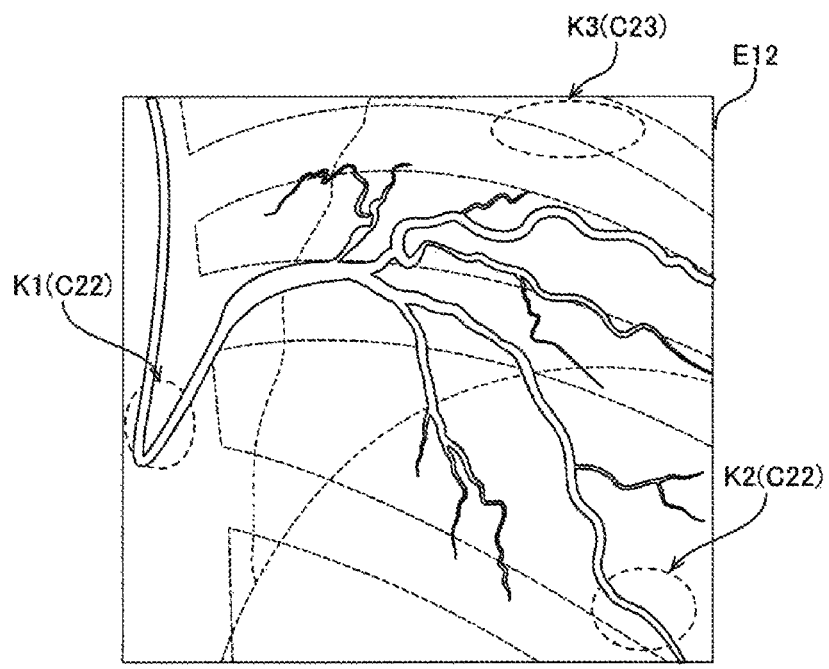
FIG. 11 is a diagram for explaining a second X-ray image in the X-ray imaging apparatus according to the second embodiment of the present invention.

As shown in FIG. 1, the X-ray imaging apparatus 200 is equipped with an image processing unit 202. In detail, as shown in FIG. 10, in the second embodiment, the image processing unit 202 acquires the first X-ray image E11 in a state in which the indwelling object R1 (for example, a balloon) to which a pair of real markers M1 and M2 which are reflected in the X-ray image by absorbing X-rays is attached is placed at the region-of-interest (stenosed segment) of the heart part of the subject P is the subject part. Then, as shown in FIG. 11, the image processing unit 202 acquires the second X-ray image E12 of the subject P after the treatment (medical treatment) is performed in the region-of-interest by the surgeon and the indwelling object R1 is removed from the subject P. Both the first X-ray image E11 and the second X-ray image E12 are each acquired as a moving image.

Here, in the second embodiment, the image processing unit 202 is configured to acquire the change of the relative position based on the movement information of the subject P (heartbeat feature points K1 to K3) with respect to the imaging unit 1 and generate the second image F12 in which a pair of virtual marker images H31 and H32 are superimposed at the corresponding position C31 and C32 (see FIG. 13) in the second X-ray image E12 reflecting the acquired relative position change. That is, by displaying the pair of virtual marker images H31 and H32, the image processing unit 202 also has a function of virtually displaying the pair of actual markers M1 and M2 also in the second image F12.

Specifically, the image processing unit 202 is configured to acquire the movement information from the position of the heartbeat feature points K1 to K3 in the subject P in the first X-ray image E11 to the position of the heartbeat feature points K11 to K13 in the subject P in the second X-ray image E12 as the movement information of the subject P and acquire the change of the relative position based on the acquired movement information. Further, the heartbeat feature points K1 to K3 each means not only one pixel (point) on the X-ray image but also a predetermined region (the region indicated by the dotted line of K1 to K3 in FIG. 10). The heartbeat feature points K1 to K3 each are an example of the "first feature point" recited in claims.

For example, the heartbeat feature points K1 to K3 include at least one of the indwelling object in the subject P and the structural object of the subject P. Specifically, the heartbeat feature points K1 to K3 include at least one of the stent, the guide wire and the catheter indwelled in the subject P or at least one of a cardiac muscle which is a structural object of the subject P and a plaque (calcified blood vessel). FIG. 10 shows an example in which the heartbeat feature point K1 is a catheter, the heartbeat feature point K2 is a guide wire, and the heartbeat feature point K3 is a myocardium.

The image processing unit 202 performs image analysis (image recognition) processing in the first X-ray image E11 to thereby detect the image value pattern corresponding to the pixel value pattern of the heartbeat feature points K1 to K3 pre-stored in the storage unit 4 on the first X-ray image E11. Then, the image processing unit 202 sets the heartbeat feature points K1 to K3 based on the detected pixel value pattern, and sets the heartbeat feature points K1 to K3 as the marker reference positions C21 to C23, respectively. The image processing unit 202 is configured to also detect the pair of real markers M1 and M2, which are feature points different from the heartbeat feature points K1 to K3 of the first X-ray image E11 by performing image analysis processing in the same manner.

Figure 12:
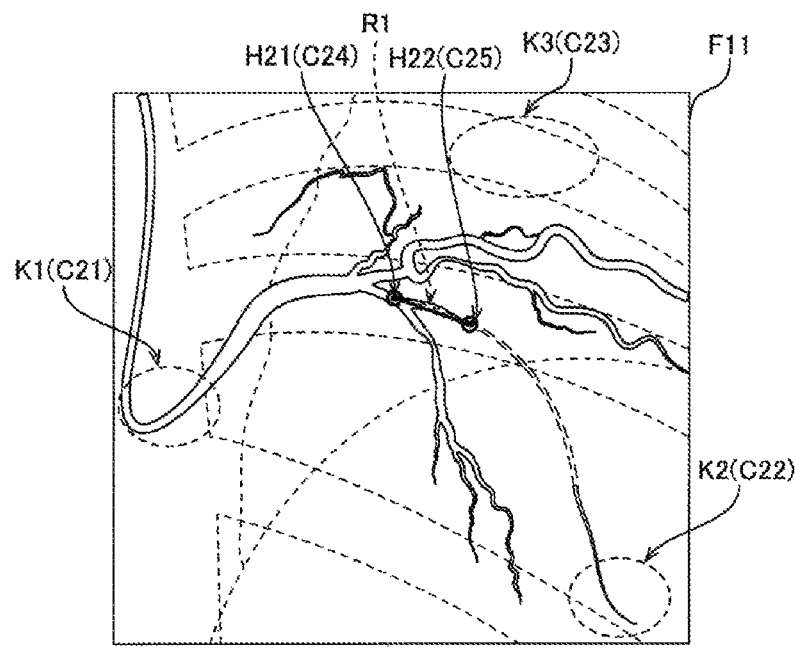
FIG. 12 is a diagram for explaining a first image in the X-ray imaging apparatus according to the second embodiment of the present invention.

The image processing unit 202 is configured to set the marker reference positions C24 and C25 based on the positions of the pair of actual markers M1 and M2 in the detected subject P. Then, as shown in FIG. 12, the image processing unit 202 is configured to generate the first image F11 in which a pair of virtual marker images H21 and H22 are displayed in a manner as to be superimposed at the positions approximately matching the marker reference positions C24 and C25.

As shown in FIG. 14, the heartbeat feature points K1 to K3 and the pair of real markers M1 and M2 are objects moving in accordance with the heartbeat, and move while tracing the same trajectory for each heartbeat (period). Then, they returns to the same positions on the X-ray image at every period of the heartbeat.

Therefore, the image processing unit 202 is configured to acquire the positions of the heartbeat feature points K1 to K3 and the pair of real markers M1 and M2 for each frame of the first X-ray image E11 as a moving image to acquire the difference value between the frames to thereby acquire the movement information (operation pattern) of the heartbeat feature points K1 to K3 and the movement information (operation pattern) of the pair of real markers M1 and M2. For example, the image processing unit 202 acquires the movement information (periodic movement information) of the heartbeat feature points K1 to K3 and the movement information (periodic movement information) of the pair of real markers M1 and M2 for one heartbeat cycle to thereby acquire the movement information of the heartbeat feature points K1 to K3 corresponding to the phase of the heartbeat and the pair of real markers M1 and M2 corresponding to the phase of the heartbeat.

For example, as shown in FIG. 14, the image processing unit 202 acquires the position information (for example, K1a, K1b, K1c, K2a, K2b, K2c, . . . , K3a, K3b, K3c . . . ) of the heartbeat feature points K1 to K3 (P1, P2, P3, . . . ) for each frame of the first X-ray image E11 and the position information (M1a, M1b, M1c, . . . , M2a, M2b, M2c . . . ) of the pair of real markers M1 and M2.

Figure 15:
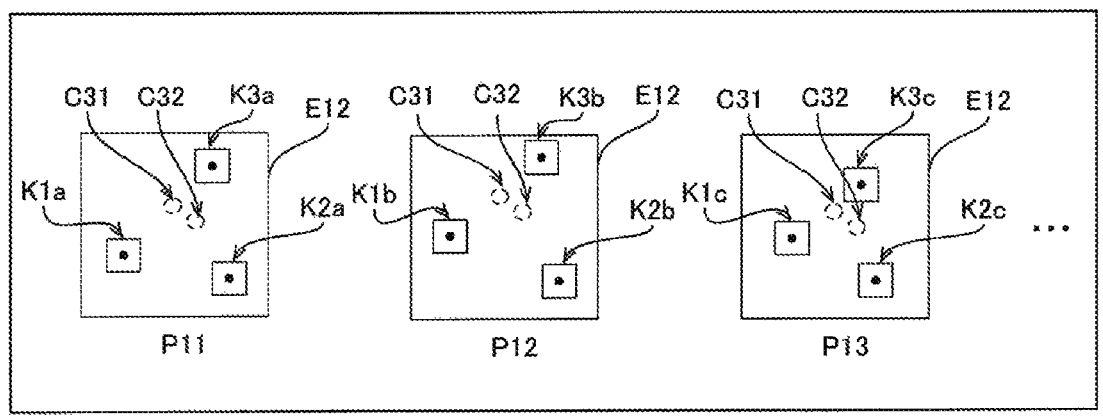
FIG. 15 is a diagram for explaining the setting of the corresponding position of the second image in the X-ray imaging apparatus according to the second embodiment of the present invention.

As shown in FIG. 15, also in the second X-ray image E12 (P11, P12, P13 . . . ) from which the indwelling object R1 having the pair of real markers M1 and M2 has been removed, the image processing unit 202 acquires periodic movement information of the heartbeat feature points K1 to K3 corresponding to the heartbeat. With this, the image processing unit 202 is configured to detect the phase of the heartbeat based on the periodic movement information of the heartbeat feature points K1 to K3, and compute corresponding positions C31 and C32 in which the pair of markers M1 and M2 are placed as the position reflecting the change of the relative position on the second X-ray image E12.

Figure 13:
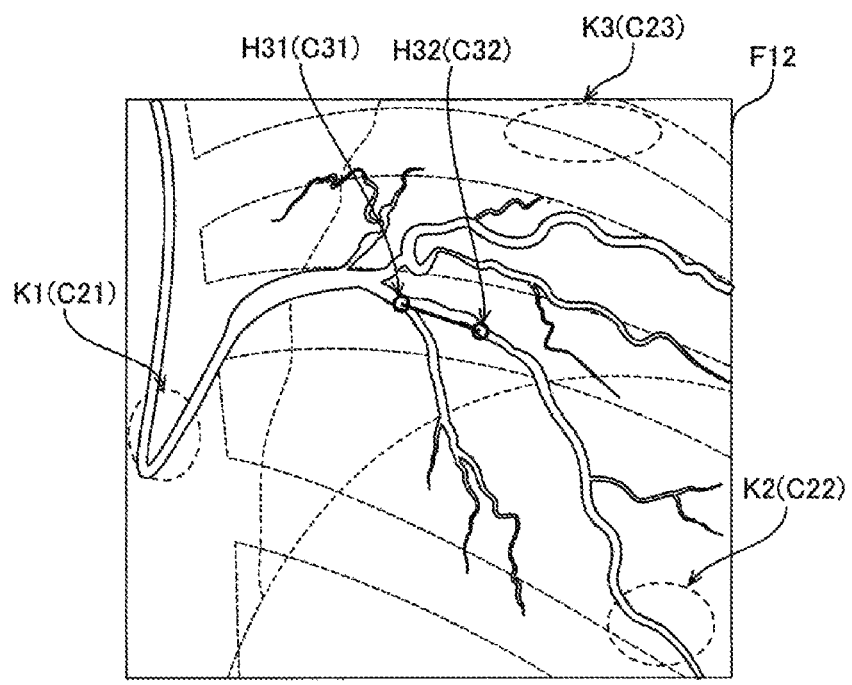
FIG. 13 is a diagram for explaining a second image of the X-ray imaging apparatus according to the second embodiment of the present invention.

Then, as shown in FIG. 13, the image processing unit 202 is configured to generate the second image F12 to be displayed on the display unit 3 in a state in which the pair of virtual marker images H31 and H32 is superimposed at the corresponding positions C31 and C32. Further, the second image F12 is a moving image, and the image processing unit 202 is configured to display the pair of virtual marker images H31 and H32 in a manner as to follow the heartbeat. Therefore, the image processing unit 202 is configured to cause a motion similar to the motion of the pair of real markers M1 and M2 moving in conjunction with the heartbeat in the pair of virtual marker images H31 and H32.

The other configurations of the second embodiment are the same as those of the first embodiment. That is, also in the image processing unit 202 according to the second embodiment, it is configured such that when at least one of the X-ray irradiation detection unit 11 and the placement unit 12 moves with respect to the other, in addition to the above image processing, it is configured to perform image processing (calculation of the change of the relative position) by the first embodiment.

(X-Ray Image Display Method by Second Embodiment)

Figure 16:
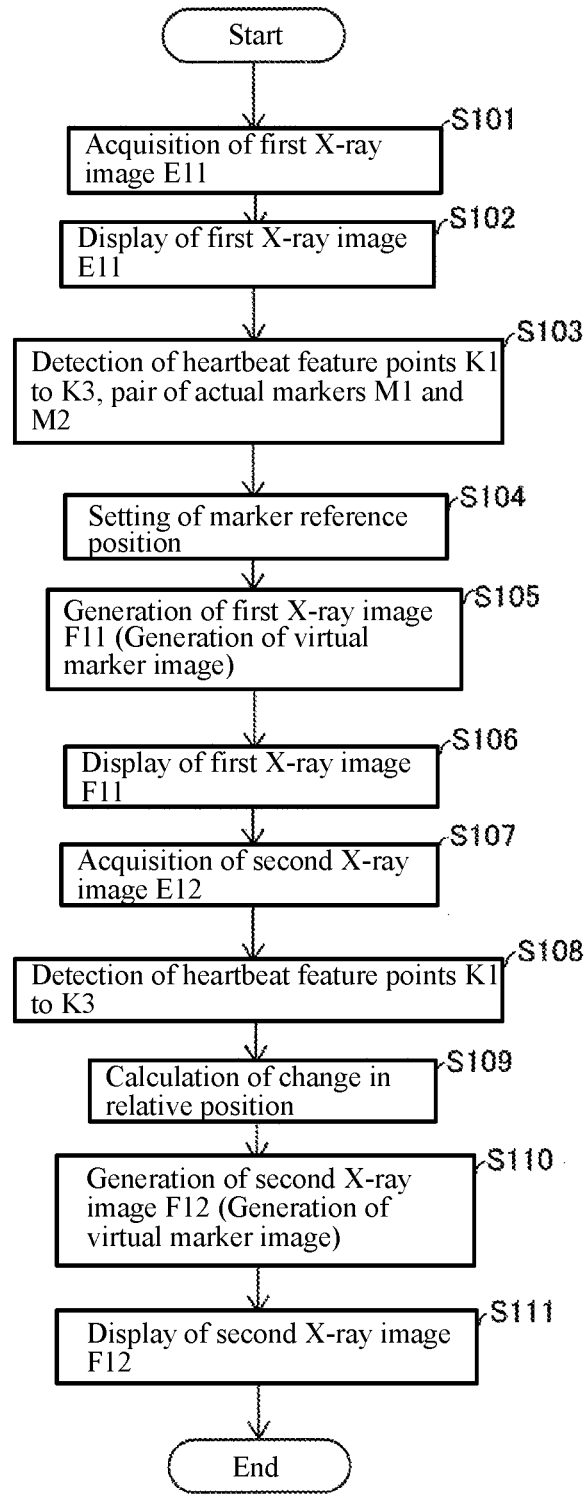
FIG. 16 is a flowchart for explaining the X-ray image display processing according to the second embodiment of the present invention.

Next, with reference to FIG. 16, an X-ray image display method (X-ray image display processing) by an X-ray imaging apparatus 200 according to the second embodiment will be described. The X-ray image display processing is executed by the image processing unit 202.

In Step S101, a first X-ray image E11 is acquired. Then, in Step S102, the first X-ray image E11 is displayed on the display unit 3. Thereafter, the process proceeds to Step S103.

In Step S103, heartbeat feature points K1 to K3 and a pair of real markers M1 and M2 on the first X-ray image E11 are detected. That is, the periodic movement information of the heartbeat feature points K1 to K3 on the first X-ray image E11 and the periodic movement information of the pair of real markers M1 and M2 are acquired. Thereafter, the process proceeds to Step S104.

In Step S104, positions corresponding to the pair of real markers M1 and M2 are set as marker reference positions C24 and C25. Thereafter, the process proceeds to Step S105.

In Step S105, a first image F11 is generated in which a pair of virtual marker images H21 and H22 are displayed at positions of the pair of real markers M1 and M2 of the first X-ray image E11 in a superimposed manner. Thereafter, the process proceeds to Step S106. In Step S106, the first image F11 is displayed on the display unit 3. Thereafter, the process proceeds to Step S107.

In Step S107, the second X-ray image E12 is acquired. Thereafter, the process proceeds to Step S108. In Step S108, the periodic movement information of the heartbeat feature points K1 to K3 on the second X-ray image E12 is acquired. Thereafter, the process proceeds to Step S109.

In Step S109, based on the periodic movement information of the heartbeat feature points K1 to K3, the change of the relative position is calculated, and the corresponding position C31 and C32 are set. Thereafter, the process proceeds to Step S110. In Step S110, a second image F12 is generated in which a pair of virtual marker images H31 and H32 are displayed at positions where the pair of real markers M1 and M2 of the second X-ray image E12 is arranged in a superimposed manner. Thereafter, the process proceeds to Step S111.

In Step S111, a second image F12 is displayed on the display unit 3. After that, the X-ray image display processing (X-ray image display method) by the second embodiment is terminated.

Effects of Second Embodiment

In the second Embodiment, the following effects can be obtained.

In the second Embodiment, the image processing unit 202 is configured to acquire the movement information from the position of the heartbeat feature points K1 to K3 in the subject P in the first X-ray image E11 to the position of the heartbeat feature points K1 to K3 in the subject P in the second X-ray image E12 as the movement information of the subject P and acquire the change of the relative position based on the acquired movement information.

As a result, even in cases where the imaging unit 1 does not move and the region-of-interest (heartbeat feature points K1 to K3) of the subject P moves with respect to the imaging unit 1, by acquiring the position of the heartbeat feature points K1 to K3 in the first image F11, the movement information of the subject P can be acquired, and therefore, the change of the relative position between the imaging unit 1 and the subject P (heartbeat feature points K1 to K3) can be acquired.

Further, in the second embodiment, as described above, the heartbeat feature points K1 to K3 include at least one of the indwelling object in the subject and the structural object of the subject. With this, at least one of the indwelling object in the subject P and the subject of the subject, which is less likely to transmit X-rays as compared with the blood vessel and is easier to be visually recognized (detected) as compared with the blood vessel on the X-ray image, is included in the heartbeat feature points K1 to K3. Therefore, it is possible to easily obtain the positions of the heartbeat feature points K1 to K3 from the first X-ray image E11.

In the second embodiment, as described above, the first image F11 is a moving image reflecting the subject P (heart) that periodically operates. The image processing unit 202 is configured to acquire the periodic movement information of the heartbeat feature points K1 to K3 in the subject P in the first image F11 and the periodic movement information of the marker reference positions C24 and C25 and acquire the change of the relative position based on the acquired periodic movement information. As a result, when X-ray imaging is performed on the periodically moving part of the subject (such as a heart part), the corresponding positions in the second X-ray image E12 can be acquired (calculated) based on the information of the periodic movement of the subject P (e.g., heartbeat) in the first X-ray image E11 and the periodic movement information of the marker reference positions C24 and C25 caused by the movement of subject P. As a result, even in cases where the subject P (region-of-interest) periodically moves, the virtual marker images H31 and H32 can be displayed at appropriate positions in the second image F12.

In the second embodiment, as described above, the image processing unit 202 is configured to generate the first image F11 in which the marker reference positions C24 and C25 are set based on the positions of the pair of real markers M1 and M2 in the subject P different from the heartbeat feature points K1 to K3 in the first X-ray image E11. Then, the image processing unit 202 is configured to acquire the periodic movement information of the heartbeat feature points K1 to K3 and the periodic movement information of the second feature point, acquire the change of the relative position based on the acquired periodic movement information, and generate the second image F12 in which the pair of virtual marker images H31 and H32 virtually displaying the pair of real markers M1 and M2 is superimposed at the corresponding positions C31 and C32 in the second X-ray image E12 having no pair of real markers M1 and M2 reflecting the change of the relative position. With this, the positions of the pair of real markers M1 and M2 in the first X-ray image E11 can be automatically set as marker reference positions C24 and C25, and the pair of virtual marker images H31 and H32 can also be displayed at positions corresponding to the pair of real markers M1 and M2 for the second image F12 having no pair of real markers M1 and M2. As a result, even in cases where there is no pair of real markers M1 and M2 in the second image F12, the positions of the pair of real markers M1 and M2 can be virtually displayed by the pair of virtual marker images H31 and H32 at appropriate positions.

In the second embodiment, as described above, the pair of real markers M1 and M2 are included in the indwelling object R1 in the subject P. With this, even in a state in which when the first X-ray image E11 is captured, the indwelling object R1 is placed in the subject P, and at the time when the second X-ray image E12 is captured, the indwelling object R1 has been removed from the subject P or before the indwelling object R1 is placed in the subject P, in the second image F12, the pair of virtual marker images H31 and H32 can virtually display the indwelling position of the indwelling object R1.

In the second embodiment, as described above, the first image F11 and the second image F12 each include an image reflecting the heart part of the subject P. With this, since the heart part of the subject P is a part of the subject P periodically repeating (heartbeat), even in cases where the subject P (region-of-interest) periodically moves, the region-of-interest can be visually recognized appropriately by the pair of virtual marker images H31 and H32.

Note that the other effects of the second embodiment are the same as those of the first embodiment.

Modified Embodiments

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the first and second embodiments, an example in which a lower limb and a heart of subject are X-ray imaged is shown, but the present invention is not limited thereto. That is, in the present invention, a portion of a subject other than a lower limit and a heart, such as, e.g., an arm portion and an abdomen of a subject, may be X-ray imaged.

In the aforementioned first and second embodiments, an example in which a human body is imaged is shown, but the present invention is not limited to this. In the present invention, the X-ray imaging apparatus may be configured to image a subject of an animal (e.g., a dog, a mouse, etc.) other than a human body.

Further, in the first embodiment, an example in which the virtual marker image is displayed at the corresponding position of the fluoroscopic image with respect to the marker reference position of the stitched image, but the present invention is not limited thereto. For example, in the present invention, the virtual marker image may be displayed at the corresponding position of the stitched image with respect to the marker reference position of the fluoroscopic image, the virtual marker image may be displayed at the corresponding position of the stitched image with respect to the marker reference position of the stitched image, and the virtual marker image may be displayed at the corresponding position of the fluoroscopic image for the marker reference position of the fluoroscopic image.

In the first embodiment, an example is shown in which a virtual marker image is superimposed on a fluoroscopic image (second X-ray image) acquired after acquiring a stitched image, while in the second embodiment, an example is shown in which a second X-ray image acquired after acquiring the first X-ray image is acquired, but the present invention is not limited thereto. That is, in the present invention, a past fluoroscopic image (second X-ray image) captured before acquiring a stitched image (first X-ray image) is read out from the storage unit and the virtual marker image may be displayed in a manner as to be superimposed on the past X-ray image (second X-ray image).

Figure 17A:
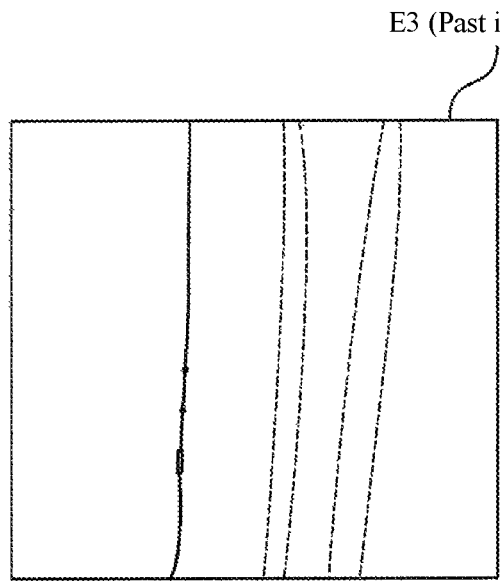
FIG. 17A is a diagram for explaining a past X-ray image in an X-ray imaging apparatus according to a first modification of the first embodiment of the present invention.
Figure 17B:
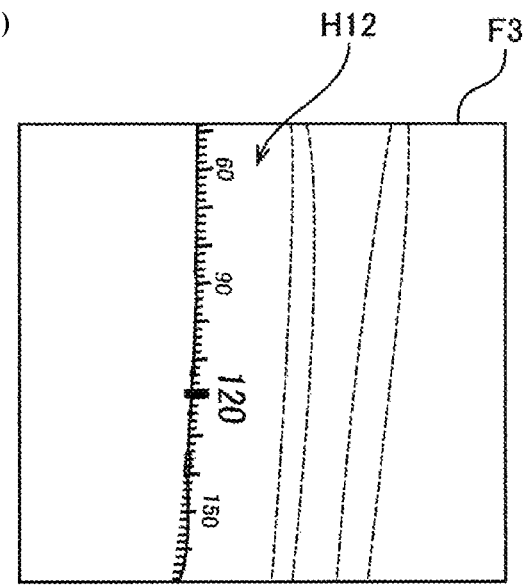
FIG. 17B is a diagram for explaining a past X-ray image in which a virtual ruler image in the X-ray imaging apparatus according to the first modification of the first embodiment of the present invention is superimposed.

Here, the image processing unit 302 (see FIG. 1) of the X-ray imaging apparatus 300 according to a first modification of the first embodiment is configured to read out a past X-ray image E3 (second X-ray image, see FIG. 17A) captured before acquiring the stitched image E1 (see FIG. 4) as a first X-ray image from the storage unit 4 (see FIG. 1) and superimpose a virtual ruler image H12 on the past X-ray image E3 (second X-ray image) to thereby generate a past fluoroscopic image F3 (see FIG. 17B).

Specifically, the image processing unit 302 is configured such that when displaying the virtual ruler image H12 in the current fluoroscopic image F2 as shown in FIG. 7, the image processing unit displays the virtual ruler image H12 away from the blood vessel (region-of-interest) (on the screen edge side), while when displaying the virtual ruler image H12 in the past fluoroscopic image F3 as shown in FIG. 17B, the image processing unit displays the virtual ruler image H12 so as to be superimposed at the position of the blood vessel (region-of-interest). This configuration of the image processing unit 302 can be realized by image-recognizing the blood vessel (region-of-interest) or the guide wire in the stitched image E1, storing the position information of the region-of-interest in the storage unit 4, and setting the display position of the virtual ruler image H12 based on the position information of -interest.

In the first and second embodiments, an example is shown in which the virtual marker image is displayed as a circular marker image, a rectangular marker image, or a virtual ruler image, but the present invention is not limited thereto. For example, the virtual marker image may be displayed as a marker image having a polygonal shape or as a marker image imitating an outline or contour shape of a stent.

In the first and second embodiments, an example is shown in which a virtual marker image is superimposed on a stitched image (first image), but the present invention is not limited thereto. That is, in the present invention, it is sufficient to display a virtual marker image on at least the fluoroscopic image (second image) in a superimposed manner, and it is not necessary to display the virtual marker image on the stitched image (first image) in a superimposed manner.

Further, in the first embodiment, an example is shown in which both of the X-ray irradiation detection unit (holder) and the placement unit (top board) are configured to be movable to acquire the change of the relative position. However, the present invention is not limited thereto. That is, in the present invention, it is sufficient that at least one of the X-ray irradiation detection unit and the placement unit can be moved.

In the first embodiment, an example is shown in which the marker reference position is set based on an input operation from an operator, but the present invention is not limited thereto. In the present invention, even in the case of imaging a lower limb portion of a subject, it may be configured to set a marker reference position based on the movement information of the feature point in the same manner as in the second embodiment. For example, the X-ray imaging apparatus may be configured such that in the case of imaging a lower limb portion, image recognition (image analysis) is performed on the structural object, such as, e.g., a blood vessel and the indwelling object in the subject, by the image processing unit, and when a predetermined feature point is detected, the position of the feature point is automatically set as a marker reference position by the image processing unit.

In the first and second embodiments, for the sake of convenience of explanation, the flow-driven type flow chart for sequentially performing the processing of the X-ray imaging apparatus of the present invention in accordance with the processing flow is described, but the present invention is not limited thereto. In the present invention, the processing operation may be performed by an event driven type (event driven type) processing that executes processing on an event basis. In this case, it may be performed in a completely event driven manner, or a combination of event driving and flow driving may be performed.

In the aforementioned first and second embodiments, an example of a configuration (single plane) provided with one X-ray irradiation detection unit is shown, but the present invention is not limited thereto. In the present invention, it may be configured to provide two X-ray irradiation detection units (biplane).

In the first embodiment, an example in which the virtual ruler image is configured to include both the scale image and the scale value image, but the present invention is not limited thereto. For example, a virtual ruler image may be constituted only by a scale image.

In the first and second embodiments, an example of the display positions of the virtual marker image and the virtual ruler image are shown, but the present invention is not limited thereto. That is, the virtual marker image and the virtual ruler image may be displayed at an arbitrary position on the image, for example, it may be displayed along the edge of the image.

In the first embodiment, an example is shown in which the virtual ruler image is displayed in a linear shape or an arc shape, but the present invention is not limited thereto. For example, the virtual ruler image may be displayed in a serpentine shape along a blood vessel shape.

Figure 18A:
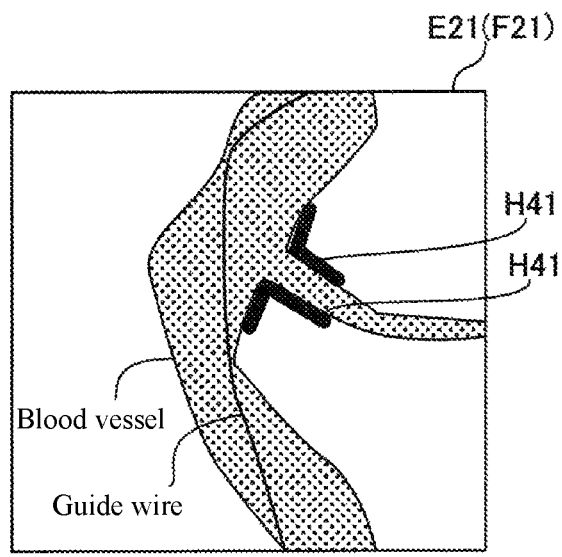
FIG. 18A is a diagram for explaining the processing (first image) of an X-ray imaging apparatus according to a second modification of the first and second embodiments of the present invention.
Figure 18B:
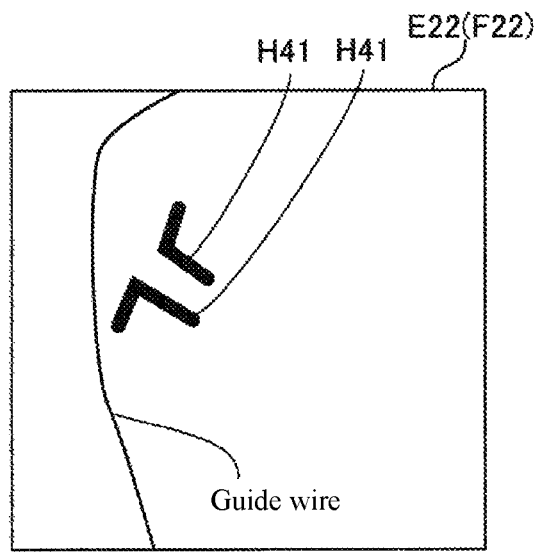
FIG. 18B is a diagram for explaining the processing (second image) of an X-ray imaging apparatus according to a second modification of the first and second embodiments of the present invention.

In the first and second embodiments, the virtual marker image and the virtual ruler image are stored in advance in the storage unit, but the present invention is not limited thereto. For example, an image processing unit 402 (see FIG. 1) of the X-ray imaging apparatus 400 according to the second modification is configured to display not an image stored in advance in the storage unit 4, but as shown in FIG. 18, an image drawn on the first X-ray image E21 as the virtual marker image H41 in the first image F21 (FIG. 18A) and the second image F22 (FIG. 18B) by an input operation (handwrite inputting) of the operation unit 5 by an operator. In this case, even in cases where the imaging range of the second X-ray image E22 is different from the imaging range of the first X-ray image E21 at the time of capturing the second X-ray image E22, in the same manner as in the first and second embodiments, the virtual marker image H41 is displayed at the corresponding position of the second image F22 by the processing of the image processing unit 402.

Further, as shown in FIG. 19, an image processing unit 502 (see FIG. 1) of the X-ray imaging apparatus 500 according to a third modification is configured to extract a border from a blood vessel image in the first X-ray image E31 and display the extracted edge image (blood vessel contour image) as a virtual marker image H42 (vascular contour emphasized image) on the first image F31 (FIG. 19A) and the second image F32 (FIG. 19B). In this case, even in cases where the imaging range of the second X-ray image E32 is different from the imaging range of the first X-ray image E31 at the time of capturing the second X-ray image E32, in the same manner as in the first and second embodiments, the virtual marker image H42 is displayed at the corresponding position of the second image F22 by the processing of the image processing unit 502.

The invention claimed is:

1. An X-ray imaging apparatus comprising:
   an imaging device that captures an X-ray image by irradiating X-rays to a subject and detecting the X-rays that have passed through the subject;
   a reference position setter that sets a marker reference position with respect to a first X-ray image;
   a marker generator that generates a first image in which a virtual marker image is superimposed at the marker reference position in the first X-ray image;
   a display that displays the first image; and
   a relative position calculator that resets the marker reference position to a position reflecting a change of a relative position between the subject and the imaging device with respect to a second X-ray image captured in which the relative position is changed,
   wherein the relative position calculator resets the marker reference position after displaying the first image,
   wherein the marker generator generates a second image in which the virtual marker image is superimposed again at the reset marker reference position, and
   wherein the second image is displayed on the display.

2. The X-ray imaging apparatus as recited in claim 1, wherein the virtual marker image includes a pair of virtual marker images.

3. The X-ray imaging apparatus as recited in claim 1, wherein the virtual marker image includes a virtual ruler image.

4. The X-ray imaging apparatus as recited in claim 1,
   wherein the relative position calculator acquires the change of the relative position based on movement information of at least one of the subject and the imaging unit, and
   wherein the marker generator generates the second image in which the virtual marker image is superimposed again at the reset marker reference position in the second X-ray image reflecting the acquired relative position change.

5. The X-ray imaging apparatus as recited in claim 4,
   wherein the imaging device includes an X-ray irradiation detection unit-device that irradiates the X-rays to the subject and detects the X-rays that have passed through the subject, and a placement device that is capable of placing the subject,
   wherein at least one of the X-ray irradiation detection device and the placement device is configured to be movable with respect to the other, and
   wherein the relative position calculator is configured to acquire the change of the relative position based on the movement information of at least one of the X-ray irradiation detection device and the placement device.

6. The X-ray imaging apparatus as recited in claim 4, further comprising:
   an image processor that includes the reference position setter, the marker generator, and the relative position calculator,
   wherein the image processor is configured to acquire the movement information as the movement information of the subject from a position of a first feature point in the subject in the first X-ray image to a position of the first feature point in the subject in the second X-ray image, and acquire the change of the relative position based on the acquired movement information.

7. The X-ray imaging apparatus as recited in claim 6, wherein the first feature point includes at least one of an indwelling object in the subject and a structural object of the subject.

8. The X-ray imaging apparatus as recited in claim 6,
   wherein the first image is a moving image reflecting the subject that periodically functions,
   wherein the image processor is configured to acquire periodic movement information of the first feature point in the subject in the first image and the periodic movement information of a marker reference position and acquire the change of the relative position based on the acquired periodic movement information.

9. The X-ray imaging apparatus as recited in claim 8, wherein the image processor is configured to generate the first image in which the marker reference position is set based on the position of a second feature point in the subject different from the first feature point in the first X-ray image, acquire the periodic movement information of the first feature point and the periodic movement information of the second feature point, acquire the change of the relative position based on the acquired periodic movement information, and generate the second image in which the virtual marker image virtually displaying the second feature point is superimposed at the reset marker reference position in the second X-ray image that does not have the second feature point reflecting the change of the relative position.

10. The X-ray imaging apparatus as recited in claim 9, wherein the second feature point includes an indwelling object in the subject.

11. The X-ray imaging apparatus as recited in claim 6, wherein the first image and the second image each include an image in which a heart part of the subject is imaged.

12. The X-ray imaging apparatus as recited in claim 1, wherein at least one of the first image and the second image is a stitched image captured at a plurality of relative positions.

13. The X-ray imaging apparatus as recited in claim 12, wherein the first image is the stitched image, and the second image is a fluoroscopic image captured at one relative position.

14. The X-ray imaging apparatus as recited in claim 12, wherein the first image and the second image each include an image in which a lower limb portion of the subject is imaged.

15. The X-ray imaging apparatus as recited in claim 1, wherein the second image is a moving image.

16. The X-ray imaging apparatus as recited in claim 1,
    wherein the first image is an image including an image of a contrast agent injected into the subject, and
    wherein the second image is an image not including the image of the contrast agent.

17. The X-ray imaging apparatus as recited in claim 1, wherein the first image includes an image in which a partial image in a moving image is displayed as a still image.

18. The X-ray imaging apparatus as recited in claim 1, further comprising:
    an operation receptor that accepts an input operation from an operator,
    wherein it is configured so that the marker reference position is set based on the input operation specifying the position on the first X-ray image displayed on the display.

19. The X-ray imaging apparatus as recited in claim 1,
    wherein the marker generator is configured to generate the second image in which a plurality of virtual marker images are superimposed on the second X-ray image, and
    wherein the relative position calculator calculates a distance between the plurality of virtual marker images.

20. The X-ray imaging apparatus as recited in claim 19, wherein it is configured to display an image indicating the distances among the plurality of virtual marker images on the display together with the second image.

21. The X-ray imaging apparatus as recited in claim 19, wherein the relative position calculator is configured to acquire magnification ratio information of the second X-ray image, and calculate distances in an actual scale among the plurality of virtual marker images based on the magnification ratio information.

22. An X-ray image display method configured to capture an X-ray image by irradiating X-rays to a subject and detecting the X-rays that have passed through the subject, process the captured X-ray image, and display the X-ray image, the method comprising:

setting a marker reference position with respect to a first X-ray image;

generating a first image in which a virtual marker image is superimposed at the marker reference position in the first X-ray image;

displaying the first image;

resetting the marker reference position to a position reflecting a change of a relative position between the subject and the imaging device with respect to a second X-ray image captured in which the relative position is changed after displaying the first image;

generating a second image in which the virtual marker image is superimposed again at the reset marker reference position; and displaying the second image.

\* \* \* \* \*